United States Patent
Nechushtai et al.

(10) Patent No.: US 11,208,443 B2
(45) Date of Patent: Dec. 28, 2021

(54) NAF-1 DERIVED PEPTIDES AND USES THEREOF

(71) Applicant: YISSUM RESEARCH DEVELOPMENT COMPANY OF THE HEBREW UNIVERSITY OF JERUSALEM LTD., Jerusalem (IL)

(72) Inventors: Rachel Nechushtai, Motza I'llit (IL); Assaf Friedler, Mevaseret Zion (IL); Anat Iosub-Amir, Jerusalem (IL); Merav Darash-Yahana, Jerusalem (IL); Yang-Sung Sohn, Modi'in (IL); Dorit Michaeli, Mevaseret Zion (IL)

(73) Assignee: YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 0 days.

(21) Appl. No.: 16/485,980

(22) PCT Filed: Feb. 12, 2018

(86) PCT No.: PCT/IL2018/050160
§ 371 (c)(1),
(2) Date: Aug. 14, 2019

(87) PCT Pub. No.: WO2018/150417
PCT Pub. Date: Aug. 23, 2018

(65) Prior Publication Data
US 2019/0375805 A1    Dec. 12, 2019

Related U.S. Application Data

(60) Provisional application No. 62/458,600, filed on Feb. 14, 2017.

(51) Int. Cl.
| | | |
|---|---|---|
| C07K 14/47 | (2006.01) | |
| A61K 38/17 | (2006.01) | |
| A61K 47/60 | (2017.01) | |
| A61P 35/00 | (2006.01) | |
| A61K 45/06 | (2006.01) | |
| A61K 38/00 | (2006.01) | |

(52) U.S. Cl.
CPC .......... *C07K 14/47* (2013.01); *A61K 38/1709* (2013.01); *A61K 45/06* (2013.01); *A61K 47/60* (2017.08); *A61P 35/00* (2018.01); *A61K 38/00* (2013.01)

(58) Field of Classification Search
CPC .... A61K 38/10; A61K 38/1709; C07K 14/47; C07K 7/08
See application file for complete search history.

(56) References Cited

U.S. PATENT DOCUMENTS

2007/0027308 A1    2/2007    Milne Edwards

FOREIGN PATENT DOCUMENTS

| WO | 2013040142 A2 | 3/2013 |
|----|---|---|
| WO | 2017168414 A1 | 10/2017 |

OTHER PUBLICATIONS

GenBank: KFO84367.1 (Year: 2014).*
Hoskin et al. "Studies on anticancer activities of antimicrobial peptides", Biochimica et Biophysica Acta, 2008, pp. 357-375 (Year: 2008).*
Baker et al. "Anticancer Efficacy of Magainin2 and Analogue Peptides" Cancer Research, 1993, 3052-3057 (Year: 1993).*
Sohn et al., "NAF-1 and mitoNEET are central to human breast cancer proliferation by maintaining mitochondrial homeostasis and promoting tumor growth", PNAS, 2013; pp. 14676-14681 (Year: 2013).*
Imura et al. "Action mechanism of tachyplesin I and effects of PEGylation", Biochimica et Biophysica Acta, 2007, pp. 1160-1169 (Year: 2007).*
Amir et al., (2015) Highly homologous proteins exert opposite biological activities by using different interaction interfaces. Sci Rep 5: 11629; 11 pages.
Amr et al., (2007) A homozygous mutation in a novel zinc-finger protein, ERIS, is responsible for Wolfram syndrome 2. Am J Hum Genet 81(4): 673-683.
Bai et al., (2015) The Fe-S cluster-containing NEET proteins mitoNEET and NAF-1 as chemotherapeutic targets in breast cancer. Proc Natl Acad Sci U S A 112(12): 3698-3703.
Barrett and Bundey (1997) Wolfram (DIDMOAD) syndrome. J Med Genet 34(10): 838-841.
Chang et al., (2010) Antagonism of Beclin 1-dependent autophagy by BCL-2 at the endoplasmic reticulum requires NAF-1. EMBO J 29(3): 606-618.
Chang et al., (2012) Bcl-2-associated autophagy regulator Naf-1 required for maintenance of skeletal muscle. Hum Mol Genet 21(10): 2277-2287.
Chen et al., (2009) Cisd2 deficiency drives premature aging and causes mitochondria-mediated defects in mice. Genes Dev 23(10): 1183-1194.
Chen et al., (2015) CISD2 associated with proliferation indicates negative prognosis in patients with hepatocellular carcinoma. Int J Clin Exp Pathol 8(10): 13725-13738.
Conlan et al., (2009) Crystal structure of Miner1: The redox-active 2Fe—2S protein causative in Wolfram Syndrome 2. J Mol Biol 392(1): 143-153.

(Continued)

*Primary Examiner* — Lianko G Garyu
(74) *Attorney, Agent, or Firm* — J.A. Lindeman & Co., PLLC

(57) ABSTRACT

The present invention provides peptides comprising a sequence derived from the human NAF-1 protein, analogs of said sequence or a retro-inverso sequence of said peptide or analog. The conjugates of such peptides are provided as well. The peptides and the conjugates of the present invention are useful in treating cancer, and in particular cancer in which the expression of NAF-1 is enhanced.

19 Claims, 12 Drawing Sheets
Specification includes a Sequence Listing.

(56) References Cited

OTHER PUBLICATIONS

Danielpur et al., (2016) GLP-1-RA Corrects Mitochondrial Labile Iron Accumulation and Improves β-Cell Function in Type 2 Wolfram Syndrome. J Clin Endocrinol Metab 101(10): 3592-3599.

Darash-Yahana et al., (2016) Breast cancer tumorigenicity is dependent on high expression levels of NAF-1 and the lability of its Fe—S clusters. Proc Natl Acad Sci U S A 113(39): 10890-10895.

Du et al., (2015) NAF-1 antagonizes starvation-induced autophagy through AMPK signaling pathway in cardiomyocytes. Cell Biol Int 39(7): 816-823.

Ge et al., (2014) Pathway analysis of genome-wide association study on serum prostate-specific antigen levels. Gene 551(1): 86-91.

Holt et al., (2016) Activation of apoptosis in NAF-1-deficient human epithelial breast cancer cells. J Cell Sci 129(1): 155-165.

Hou et al., (2007) Crystallographic studies of human MitoNEET. J Biol Chem 282(46): 33242-33246.

Lin et al., (2007) Crystal structure of human mitoNEET reveals distinct groups of iron sulfur proteins. Proc Natl Acad Sci U S A 104(37): 14640-14645.

Lipper et al., (2015) Cancer-Related NEET Proteins Transfer 2Fe—2S Clusters to Anamorsin, a Protein Required for Cytosolic Iron-Sulfur Cluster Biogenesis. PLoS One 10(10): e0139699; 15 pages.

Liu et al., (2014) CISD2 expression is a novel marker correlating with pelvic lymph node metastasis and prognosis in patients with early-stage cervical cancer. Med Oncol 31(9): 183; 12 pages.

Paddock et al., (2007) MitoNEET is a uniquely folded 2Fe 2S outer mitochondrial membrane protein stabilized by pioglitazone. Proc Natl Acad Sci U S A 104(36): 14342-14347.

Salem et al., (2012) Mitochondrial biogenesis in epithelial cancer cells promotes breast cancer tumor growth and confers autophagy resistance. Cell Cycle 11(22): 4174-4180.

Sohn et al., (2013) NAF-1 and mitoNEET are central to human breast cancer proliferation by maintaining mitochondrial homeostasis and promoting tumor growth. Proc Natl Acad Sci U S A 110(36): 14676-14681.

Tamir et al., (2013) Nutrient-deprivation autophagy factor-1 (NAF-1): biochemical properties of a novel cellular target for anti-diabetic drugs. PLoS One 8(5): e61202; 7 pages.

Tamir et al., (2014) Integrated strategy reveals the protein interface between cancer targets Bcl-2 and NAF-1. Proc Natl Acad Sci U S A 111(14): 5177-5182.

Tamir et al., (2014) A point mutation in the [2Fe—2S] cluster binding region of the NAF-1 protein (H114C) dramatically hinders the cluster donor properties. Acta Crystallogr D Biol Crystallogr 70(Pt 6): 1572-1578.

Tamir et al., (2015) Structure-function analysis of NEET proteins uncovers their role as key regulators of iron and ROS homeostasis in health and disease. Biochim Biophys Acta 1853(6): 1294-1315.

Urano (2016) Wolfram Syndrome: Diagnosis, Management, and Treatment. Curr Diab Rep 16(1): 6; 8 pages.

Van Regenmortel and Muller (1998) D-peptides as immunogens and diagnostic reagents. Curr Opin Biotechnol 9(4): 377-382.

Vento et al., (2010) Praf2 is a novel Bcl-xL/Bcl-2 interacting protein with the ability to modulate survival of cancer cells. PLoS One 5(12): e15636; 13 pages.

Wang et al., (2015) Role of mitochondrial dysfunction and dysregulation of Ca(2+) homeostasis in insulin insensitivity of mammalian cells. Ann N Y Acad Sci 1350: 66-76.

Wang et al., (2016) Overexpressed CISD2 has prognostic value in human gastric cancer and promotes gastric cancer cell proliferation and tumorigenesis via AKT signaling pathway. Oncotarget 7(4): 3791-3805.

Wiley et al., (2013) Wolfram Syndrome protein, Miner1, regulates sulphydryl redox status, the unfolded protein response, and Ca2+ homeostasis. EMBO Mol Med 5(6): 904-918.

Wu et al., (2012) A persistent level of Cisd2 extends healthy lifespan and delays aging in mice. Hum Mol Genet 21(18): 3956-3968.

Yang et al., (2016) A novel prognostic score model incorporating CDGSH iron sulfur domain2 (CISD2) predicts risk of disease progression in laryngeal squamous cell carcinoma. Oncotarget 7(16): 22720-22732.

Yoshihara et al., (2014) Thioredoxin/Txnip: redoxisome, as a redox switch for the pathogenesis of diseases. Front Immunol 4: 514; 9 pages.

\* cited by examiner

SEQUENCE LISTING

```
<160> NUMBER OF SEQ ID NOS: 22

<210> SEQ ID NO 1
<211> LENGTH: 24
<212> TYPE: PRT
<213> ORGANISM: Homo Sapience

<400> SEQUENCE: 1

Phe Leu Gly Val Leu Ala Leu Leu Gly Tyr Leu Ala Val Arg Pro Phe
1               5                   10                  15

Leu Pro Lys Lys Lys Gln Gln Lys
            20

<210> SEQ ID NO 2
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (10)..(10)
<223> OTHER INFORMATION: D-amino acid
<220> FEATURE:
<221> NAME/KEY: MOD_RES
<222> LOCATION: (16)..(16)
<223> OTHER INFORMATION: D-amino acid
<220> FEATURE:
```

```
<221> NAME/KEY: MOD_RES
<222> LOCATION: (20)..(20)
<223> OTHER INFORMATION: D-amino acid

<400> SEQUENCE: 2

Phe Leu Gly Val Leu Ala Leu Leu Gly Tyr Leu Ala Val Arg Pro Phe
1               5                   10                  15

Leu Pro Lys Lys Lys Gln Gln Lys
            20

<210> SEQ ID NO 3
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(24)
<223> OTHER INFORMATION: D-amino acid

<400> SEQUENCE: 3

Phe Leu Gly Val Leu Ala Leu Leu Gly Tyr Leu Ala Val Arg Pro Phe
1               5                   10                  15

Leu Pro Lys Lys Lys Gln Gln Lys
            20

<210> SEQ ID NO 4
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(24)
<223> OTHER INFORMATION: D-amino acid

<400> SEQUENCE: 4

Lys Gln Gln Lys Lys Lys Pro Leu Phe Pro Arg Val Ala Leu Tyr Gly
1               5                   10                  15

Leu Leu Ala Leu Val Gly Leu Phe
            20

<210> SEQ ID NO 5
<211> LENGTH: 23
<212> TYPE: PRT
<213> ORGANISM: Homo sapiens

<400> SEQUENCE: 5

Phe Leu Gly Val Leu Ala Leu Leu Gly Tyr Leu Ala Val Arg Pro Phe
1               5                   10                  15

Leu Pro Lys Lys Lys Gln Gln
            20

<210> SEQ ID NO 6
<211> LENGTH: 22
<212> TYPE: PRT
<213> ORGANISM: Homo Sapience

<400> SEQUENCE: 6

Phe Leu Gly Val Leu Ala Leu Leu Gly Tyr Leu Ala Val Arg Pro Phe
1               5                   10                  15

Leu Pro Lys Lys Lys Gln
            20
```

<210> SEQ ID NO 7
<211> LENGTH: 21
<212> TYPE: PRT
<213> ORGANISM: Homo Sapience

<400> SEQUENCE: 7

Phe Leu Gly Val Leu Ala Leu Leu Gly Tyr Leu Ala Val Arg Pro Phe
1               5                   10                  15

Leu Pro Lys Lys Lys
            20

<210> SEQ ID NO 8
<211> LENGTH: 20
<212> TYPE: PRT
<213> ORGANISM: Homo Sapience

<400> SEQUENCE: 8

Phe Leu Gly Val Leu Ala Leu Leu Gly Tyr Leu Ala Val Arg Pro Phe
1               5                   10                  15

Leu Pro Lys Lys
            20

<210> SEQ ID NO 9
<211> LENGTH: 19
<212> TYPE: PRT
<213> ORGANISM: Homo Sapience

<400> SEQUENCE: 9

Phe Leu Gly Val Leu Ala Leu Leu Gly Tyr Leu Ala Val Arg Pro Phe
1               5                   10                  15

Leu Pro Lys

<210> SEQ ID NO 10
<211> LENGTH: 18
<212> TYPE: PRT
<213> ORGANISM: Homo Sapience

<400> SEQUENCE: 10

Phe Leu Gly Val Leu Ala Leu Leu Gly Tyr Leu Ala Val Arg Pro Phe
1               5                   10                  15

Leu Pro

<210> SEQ ID NO 11
<211> LENGTH: 17
<212> TYPE: PRT
<213> ORGANISM: Homo Sapience

<400> SEQUENCE: 11

Phe Leu Gly Val Leu Ala Leu Leu Gly Tyr Leu Ala Val Arg Pro Phe
1               5                   10                  15

Leu

<210> SEQ ID NO 12
<211> LENGTH: 23
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(23)
<223> OTHER INFORMATION: D-amino acid

<400> SEQUENCE: 12

Phe Leu Gly Val Leu Ala Leu Leu Gly Tyr Leu Ala Val Arg Pro Phe
1               5                   10                  15

Leu Pro Lys Lys Lys Gln Gln
            20

<210> SEQ ID NO 13
<211> LENGTH: 22
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(22)
<223> OTHER INFORMATION: D-amino acid

<400> SEQUENCE: 13

Phe Leu Gly Val Leu Ala Leu Leu Gly Tyr Leu Ala Val Arg Pro Phe
1               5                   10                  15

Leu Pro Lys Lys Lys Gln
            20

<210> SEQ ID NO 14
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(21)
<223> OTHER INFORMATION: D-amino acid

<400> SEQUENCE: 14

Phe Leu Gly Val Leu Ala Leu Leu Gly Tyr Leu Ala Val Arg Pro Phe
1               5                   10                  15

Leu Pro Lys Lys Lys
            20

<210> SEQ ID NO 15
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(20)
<223> OTHER INFORMATION: D-amino acid

<400> SEQUENCE: 15

Phe Leu Gly Val Leu Ala Leu Leu Gly Tyr Leu Ala Val Arg Pro Phe
1               5                   10                  15

Leu Pro Lys Lys
            20

<210> SEQ ID NO 16
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(19)

<223> OTHER INFORMATION: D-amino acid

<400> SEQUENCE: 16

Phe Leu Gly Val Leu Ala Leu Leu Gly Tyr Leu Ala Val Arg Pro Phe
1               5                   10                  15

Leu Pro Lys

<210> SEQ ID NO 17
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(18)
<223> OTHER INFORMATION: D-amino acid

<400> SEQUENCE: 17

Phe Leu Gly Val Leu Ala Leu Leu Gly Tyr Leu Ala Val Arg Pro Phe
1               5                   10                  15

Leu Pro

<210> SEQ ID NO 18
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(17)
<223> OTHER INFORMATION: D-amino acid

<400> SEQUENCE: 18

Phe Leu Gly Val Leu Ala Leu Leu Gly Tyr Leu Ala Val Arg Pro Phe
1               5                   10                  15

Leu

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide

<400> SEQUENCE: 19

Phe Leu Gly Val Leu Ala Leu
1               5

<210> SEQ ID NO 20
<211> LENGTH: 24
<212> TYPE: PRT
<213> ORGANISM: Artificial Sequence
<220> FEATURE:
<223> OTHER INFORMATION: Synthetic peptide

<400> SEQUENCE: 20

Ala Ala Gly Val Leu Ala Leu Leu Gly Tyr Leu Ala Val Arg Pro Phe
1               5                   10                  15

Leu Pro Lys Lys Lys Gln Gln Lys
            20

<210> SEQ ID NO 21
<211> LENGTH: 24

```
<212> TYPE: PRT
<213> ORGANISM: Artificial Sequence
<220> FEATURE:
<223> OTHER INFORMATION: Synthetic peptide

<400> SEQUENCE: 21

Ala Ala Gly Val Ala Ala Leu Leu Gly Tyr Leu Ala Val Arg Pro Phe
1               5                   10                  15

Leu Pro Lys Lys Lys Gln Gln Lys
            20

<210> SEQ ID NO 22
<211> LENGTH: 24
<212> TYPE: PRT
<213> ORGANISM: Artificial Sequence
<220> FEATURE:
<223> OTHER INFORMATION: Synthetic peptide

<400> SEQUENCE: 22

Phe Leu Gly Val Ala Ala Ala Leu Gly Tyr Leu Ala Val Arg Pro Phe
1               5                   10                  15

Leu Pro Lys Lys Lys Gln Gln Lys
            20
```

NAF-1 DERIVED PEPTIDES AND USES THEREOF

SEQUENCE LISTING

The Sequence Listing submitted herewith is an ASCII text file (2021-07-02 Sequence_Listing.text, created on Jul. 2, 2021, 7285 bytes) via EFS-Web is hereby incorporated by reference.

FIELD OF THE INVENTION

The present invention is directed to peptides derived from human NAF-1 protein, analogs thereof and their use in treating various types of cancer.

BACKGROUND OF THE INVENTION

Nutrient-deprivation autophagy factor-1 (NAF-1, CISD2) is a unique iron-sulfur (2Fe-2S) protein that belongs to the NEET protein family and is encoded by the CISD2 gene in humans. Recent studies implicated NAF-1, localized in endoplasmic reticulum (ER) and mitochondrial outer membranes, in a diverse array of biological processes and diseases such as regulation of autophagy, apoptosis, iron and reactive oxygen species (ROS) homeostasis and cancer. Enhanced expression of NAF-1, is associated with different cancers including breast, prostate, gastric, cervical, liver, and laryngeal cancer (Holt et al., 2015, Journal of Cell Science, 129, 155-165; Sohn, Y.-S. et al., 2013, *Proc. Natl. Acad. Sci.* USA, 110, 14676-14681; Ge, Y. Z. et al., 2014, Gene, 551, 86-91; Wang, L. et al., 2015, Oncotarget 7, 3791-3805; Liu, L. et al., 2014, Med. Oncol., 31, 183; Chen, B. et al., 2015, Int. J. Clin. Exp. Pathol. 8, 13725-13738; Yang, L. et al., 2016, Oncotarget, 7, 22720-22732). Reduction of NAF-1 expression in breast, or gastric cancer cells significantly inhibited cellular proliferation and tumorigenicity, whereas overexpression of NAF-1 in these cells significantly enhanced cellular proliferation. Darash-Yahana et al., (PNAS, 2016, 113(39), 10890-10895) showed that NAF-1 overexpression in xenograft tumors results in a dramatic augmentation in tumor size and aggressiveness and that at least two different components are required for NAF-1 to promote breast cancer tumorigenicity: high levels of NAF-1 protein expression and a unique 2Fe-2S cluster coordination structure (3Cys:1His), that conveys cluster lability.

Development of a therapy for cancer is a tedious task requiring constant search for novel targets as well as generation of novel therapeutic agents affecting these targets. There is a clear and constant need in developing of both directions and in particular in providing novel therapeutic agents for treating cancer.

SUMMARY OF THE INVENTION

The present invention is based in part on the observation that peptides derived from a specific region in the human NAF-1 protein, selectively penetrated into cancer cells and kill them.

In one aspect, the present invention provides a peptide comprising:

(a) the amino acid sequence FLGVLALLGYLAVRP-FLPKKKQQK as set forth in SEQ ID NO: 1;

(b) an analog of (a);
(c) a retro-inverso sequence of (a) or (b); or
(d) a fragment consisting of 17 to 23 consecutive amino acids of (a), (b) or (c),
wherein the peptide consists of 17 to 50 amino acids.

According to some embodiments, the peptide comprises SEQ ID NO: 1. According to a specific embodiment, the peptide consists of SEQ ID NO: 1.

According to another embodiment, the peptide comprises an analog of SEQ ID NO: 1, wherein said analog comprises from 1 to 6 amino acid substitutions, deletions or additions. According to some embodiments, the analog comprises 1-3 amino acid substitutions, deletions or additions. According to some embodiments, at least one amino acid substitution is a conservative substitution. According to other embodiments, all amino acid substitutions are conservative substitutions. According to some embodiments, at least one amino acid substitution is into the corresponding D-amino acid. According to yet other embodiments, the analog comprises the amino acid sequence of SEQ ID NO: 1, with 1 to 3 substitutions of amino acid residues into their D-amino acid residues. According to one embodiment, the peptide comprises the amino acid sequence FLGVLALLGyLAVRP-fLPKkKQQK as set forth in SEQ ID NO: 2. According to another embodiment, the peptide consists of SEQ ID NO: 2. According to some embodiments, the peptide comprises a sequence of all D-amino acids. According to a further embodiment, the peptide comprises the amino acid sequence flgvlallgylavrpflpkkkqqk as set forth in SEQ ID NO: 3. According to another embodiment, the peptide consists of SEQ ID NO: 3. According to yet other embodiments, the peptide comprises a retro-inverso sequence of any one of SEQ ID NO: 1, SEQ ID NO: 2 or SEQ ID NO: 3, or of an analog thereof. According to certain embodiments, the peptide comprises the amino acid sequence kqqkkkplfprvalygl-lalvglf as set forth in SEQ ID NO: 4.

According to a further embodiment, the peptide comprises a fragment of 17 to 23 consecutive amino acid residues of a sequence selected from SEQ ID NO: 1, analog of SEQ ID NO: 1, SEQ ID NO: 2, 3, 4 and retro-inverso sequence of an analog of SEQ ID NO: 1. According to one embodiment, the peptide comprises an amino acid sequence selected from SEQ ID Nos: 5, 6, 7, 8, 9, 10, 11, 12, 13, 14, 15, 16, 17 and 18.

According to some specific embodiments, the peptide consists of a an amino acid sequence selected from: SEQ ID NO: 1, SEQ ID NO: 2, SEQ ID NO: 3, and SEQ ID NO: 4. According to one embodiment, the peptide fragment consists an amino acid sequence selected from SEQ ID Nos: 5, 6, 7, 8, 9, 10, 11, 12, 13, 14, 15, 16, 17 and 18.

According to some embodiments, the peptide consists of from 17 to 24 amino acid residues.

According to another aspect, the present invention provides a conjugate of a peptide of the present invention with another moiety. According to some embodiment, the conjugate comprises at least one polyethylene glycol (PEG) molecule and a peptide comprising an amino acid selected from SEQ ID NOs: 1, 2, 3 and 4. According to one embodiment, the PEG molecule has a molecular weight between 350 to 1,000 Da.

According to a specific embodiment, the conjugate comprises a peptide selected from and a PEG moiety conjugated to at least one of its termini.

According to some aspects, the present invention provides a pharmaceutical composition comprising at least one peptide or at least one conjugate of the present invention. According to some embodiments, the pharmaceutical composition comprises a peptide of 17-50 amino acids comprising:

(a) the amino acid sequence FLGVLALLGYLAVRP-FLPKKKQQK as set forth in SEQ ID NO: 1;
(b) an analog of (a);
(c) a retro-inverso sequence of (a) or (b); or
(d) a fragment consisting of 17 to 23 consecutive amino acids of (a), (b) or (c); and optionally a molecule connected to said peptide to form a conjugate.

According to some embodiments, the pharmaceutical composition comprises at least one peptide comprising an amino acid sequence selected from SEQ ID NO:1, 2, 3, and 4. According to some embodiments, the pharmaceutical composition comprises at least one peptide consisting of an amino acid sequence selected from SEQ ID NO:1, 2, 3, and 4. According to some embodiments, the pharmaceutical composition comprises at least one peptide comprising an amino acid sequence selected from SEQ ID Nos: 5, 6, 7, 8, 9, 10, 11, 12, 13, 14, 15, 16, 17 and 18. According to other embodiments, the pharmaceutical composition comprises at least one conjugate of said peptide, e.g. a PEG conjugate. According to some specific embodiments, the pharmaceutical composition comprises a peptide selected from SEQ ID Nos: 1, 2, 3, 4, 5, 6, 7, 8, 9, 10, 11, 12, 13, 14, 15, 16, 17 and 18, conjugated to at least one PEG molecule.

According to another aspect, the pharmaceutical composition of the present invention is for use in treating cancer. According to some embodiments, the cancer is associated with an enhanced expression of NAF-1 protein. According to another embodiment, the cancer is selected from breast, prostate, gastric, cervical, liver, pancreas, head, neck and laryngeal cancer.

According to a further aspect, the present invention provides a method for treating cancer in a subject in need thereof comprising administering to said subject a peptide, a conjugate or a pharmaceutical composition of the present invention. According to one embodiment, the pharmaceutical composition comprises an effective amount of the peptide or of the conjugate of the present invention. The pharmaceutical composition may be administered using any suitable method. According to some embodiments, the pharmaceutical composition is administered parenterally, for example intravenously, intradermally, intramuscularly, intraperitoneally, subcutaneously, ocularly, sublingually, intranasally, by inhalation, intraspinally, intracerebrally, and transdermally. According to some embodiments, the pharmaceutical composition is administered intratumorally. According to some specific embodiments, the pharmaceutical composition is administered intratumorally during surgery.

BRIEF DESCRIPTION OF THE FIGURES

FIG. 6 shows cell uptake of fluorescein-labeled peptide of SEQ ID NO: 1 (PEP-FL) into normal (MCF-10A) or malignant (MDA-MB-231) cells and its effect on the cells' mitochondria and nuclei.

DETAILED DESCRIPTION OF THE INVENTION

Figure 1:
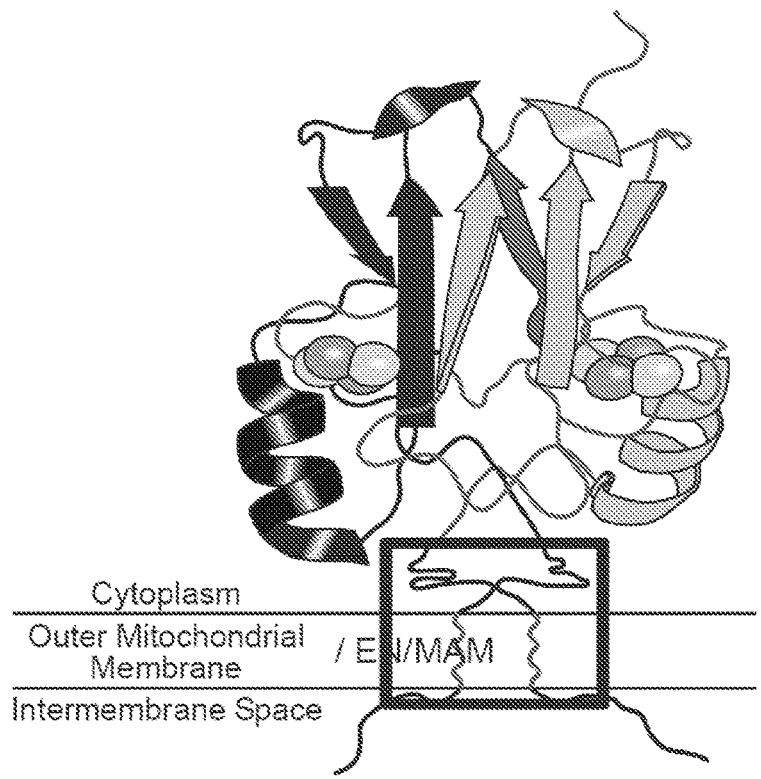
FIG. 1 shows the approximate location (outlined by a rectangle) of the peptide having amino acid sequence SEQ ID NO: 1 in the human NAF-1: spanning the mitochondrial membrane and extending to the cytoplasm.

According to one aspect, the present invention provides a peptide comprising:
(a) an amino acid sequence FLGVLALLGYLAVRP-FLPKKKQQK (SEQ ID NO: 1)
(b) an analog of (a);
(c) a retro-inverso sequence of (a) or (b); or
(d) an fragment consisting of 10 to 23 consecutive amino acids of (a), (b) or (c).

According to one embodiment, the fragment consists of 17 to 23 consecutive amino acids of (a), (b) or (c).

According to one embodiment, the peptide consists of 10 to 50 amino acids. According to another embodiment, the peptide consists of 17 to 50 amino acids.

The term "peptide" as used herein refers to a short chain of amino acid monomers linked by peptide bonds, i.e., the covalent bond formed between carboxyl group of one amino acid and an amino group of another amino acid. Peptides usually comprise up to 50 amino acids. According to some embodiments, the peptide consists of 12 to 45 amino acids. According to another embodiment, the peptide consists of 15 to 40 amino acids. According to some embodiments, the peptide comprises 17 to 35 amino acids. According to other embodiments, the peptide consists of 20 to 30 amino acids. According to another particular embodiment, the peptide consists of 17 to 24 amino acids. According to some embodiments, the peptide consists of 17 to 23, 18 to 23, or 19 to 22, or 20 to 20 amino acids.

According to any one of the above embodiments, the peptide comprises the amino acid sequence FLGV-LALLGYLAVRPFLPKKKQQK (SEQ ID NO: 1).

It is a well-known fact that a short peptide when extracted from the content of the protein most likely loses its structure and native activity. The peptide having the amino acid sequence SEQ ID NO:1 has no defined structure in saline as was shown in Example 9. The peptide of SEQ ID NO: 1 corresponds to amino acids 44-67 of human NAF-1 which are part of the transmembranal domain and the adjacent cytoplasmic region of human NAF-1 (see e.g. Example 1). This region of the protein is not involved in the coordination of the 2Fe-2S cluster of NAF-1, which, as estimated, plays a key role in tumorigenicity associated with NAF-1. It was shown in Example 4 that mitochondria and nuclei of malignant but not normal cell disappeared upon contact with the peptide of SEQ ID NO: 1.

According to another embodiment, the peptide of the present invention comprises an analog of SEQ ID NO: 1. The term "analog" refers to an amino acid sequence in which at least one amino acid of the parent sequence is modified when retaining the functionality of the parent peptide. Examples of such modifications of amino acid sequence are substitutions, rearrangements, deletions, additions and/or chemical modifications in the amino acid sequence of the parent peptide.

The term "amino acid" includes both "natural" and "unnatural" or "non-natural" amino acids.

According to one embodiment, the analog comprises at least one modification selected from a substitution, deletion and addition. According to some embodiments, the modification is a substitution. According to one embodiment, the substitution is a conservative substitution.

The term "conservative substitution" as used herein denotes the replacement of an amino acid residue by another, without altering the overall conformation and biological activity of the peptide, including, but not limited to, replacement of an amino acid with one having similar properties (such as, for example, polarity, hydrogen bonding potential, acidic, basic, shape, hydrophobic, aromatic, and the like). Amino acids with similar properties are well known in the art. For example, according to one table known in the art, the following six groups each contain amino acids that are conservative substitutions for one another: (1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W).

According to some embodiments, the substitution is not limited to natural amino acids and may be effected with non-natural amino acids. The term "non-natural amino acids" refers to amino acids having structures different from those of natural amino acid species. In one embodiment, the non-natural amino acid is a D-amino acid. Another examples of non-natural amino acids include ornithine, 3-substituted tyrosine, azidoalanine, azidohomoalanine, norleucine, norvaline, 4-aminotryptophan, 7-azatryptophan, 6-methyltryptophan, acetyllysine, ε-Boc-lysine, ε-methyllysine, 1-naphthylalanine, 2-naphthylalanine, styrylalanine, diphenylalanine, thiazolylalanine, 2-pyridylalanine, 3-pyridylalanine, 4-pyridylalanine, anthrylalanine, 2-amino-5-hexynoic acid, furylalanine, benzothienylalanine, thienylalanine, allylglycine, propargylglycine, phosphorylserine, phosphorylthreonine, and 2,3-diaminopropionic acid.

According to some embodiments, the analog comprises from 1 to 10, 2 to 8, or 3 to 6 modifications. According to one embodiment, the analog comprises from 1 to 6 modifications or 1 to 3 modifications. According to another embodiment, the analog comprises 1, 2, 3, 4, 5 or 6 modifications. According to some embodiments, the modification is a substitution, such as a conservative substitution. According to one embodiment, the analog comprises 1 to 6 conservative substitutions.

According to some embodiments, the analog comprises the amino acid sequence FLGVLAL as set forth in SEQ ID NO: 19.

According to one embodiment, the peptide analog has at least 75%, at least 80%, at least 85, at least 90%, at least 95%, at least 96% identity to the sequences selected from SEQ ID NO: 1.

According to one embodiment, the analog comprises amino acid sequence SEQ ID NO: 1 or a modified SEQ ID NO: 1 in which at least one Lys residue is substituted by another positively charged amino acid. According to one embodiment, at least one of the Lys residues is substituted by Arg.

According to any one of the above embodiments, the analog comprises a parent sequence or a modified parent sequence in which at least one of the Phe or Tyr amino acids are substituted by an amino acid with a bulky hydrophobic residue. In one embodiment, $^{1}$Phe and/or $^{16}$Phe is substituted with Tyr or Trp. According to another embodiment, $^{10}$Tyr is substituted by Phe or Trp. According to a further embodiment, $^{1}$Phe and/or $^{16}$Phe is substituted with Tyr or Trp, and $^{10}$Tyr is substituted by Phe or Trp. As used herein, the superscript number to the left of the amino acid name represents its sequential number in SEQ ID NO: 1. For Example $^{10}$Tyr or $^{10}$Y refers to the tyrosine at the $10^{th}$ position of SEQ ID NO: 1.

According to any one of the above embodiments, the analog comprises a parent sequence or a modified patent sequence in which at least one of the hydrophobic amino acid residues is substituted by Ala.

According to any one of the above embodiments, the analog comprises a parent sequence or a modified patent sequence in which [14]Arg is substituted by Ala.

According to any one of the above embodiments, the modification may be a substitution by a non-natural amino acid as defined above. According to one embodiment, the non-natural amino acid is a D-amino acid. The term "D-amino acid" refers to an amino acid having the D-configuration around the α-carbon as opposite to native L-amino acid having L-conformation. As used herein, the D-amino acid in the sequence is represented by a lower case letter, whereas the L-amino acid by a capital letter. As such, the sequence of VyL represent a sequence in which Val and Leu are native L-amino acids and Tyr is a D-amino acid.

According to any one of the above embodiments, the analog of SEQ ID NO: 1 comprises at least one D-amino acid. According to another embodiment, the analog comprises from 1 to 24, 2 to 23, 3 to 22, 4 to 21, 5 to 20, 6 to 19, 7 to 18, 8 to 17, 9 to 16, 10 to 15, 11 to 14 or 12 to 13 D-amino acids. According to one embodiment, the analog comprises 1, 2 or 3 D-amino acids. According to one embodiment, the analog comprises 4, 5 or 6 D-amino acids. According to some embodiments, at least one of the amino acids at positions 10, 16 and 20 of SEQ ID NO: 1 is D-amino acid. According to a further embodiment, at least one of [10]Y, [16]F and [20]K is a D-amino acid. According to yet another embodiment, the amino acids [10]Y, [16]F and [20]K are D-amino acids. According to one embodiment, the analog has the amino acid sequence FLGVLALLGyLAVRPfLPKkKQQK (SEQ ID NO: 2). Thus in one embodiment, the peptide comprises the amino acid sequence FLGVLALLGyLAVRPfLPKkKQQK.

According to some embodiments, the analog comprises at least 4 D-amino acids. According to another embodiment, the analog comprises at least 5, at least 6 or at least 8 D-amino acids. According to one embodiments, all amino acids of the analog are D-amino acids. According to yet another embodiment, the analog comprises the amino acid sequence in which all amino acids of SEQ ID NO: 1 are substituted by corresponding D-amino acids. Thus in one embodiment, the analog has the amino acid sequence flgvlallgylavrpflpkkkqqk (SEQ ID NO: 3) and the peptide comprises the amino acid sequence SEQ ID NO: 3. According to one embodiment, all residues of such a peptide are D-amino acids.

According to some embodiments, the peptide comprises a retro-inverso sequence of SEQ ID NO: 1. According to some embodiments, the peptide comprises the amino acid sequence kqqkkkplfprvalygllalvglf (SEQ ID NO: 4). According to other embodiments, the peptide comprises a retro-inverso sequence of and analog of SEQ ID NO: 1. According to one embodiment, all amino acids of the peptide comprising the retro-inverso sequence of any one of the above embodiments, are D-amino acids.

The terms "retro-inverso peptide" and "retro-inverse peptide" are used herein interchangeably and refer to a reverse peptide composed of D-amino acids (retro=reversed; as described in Regenmortel and Muller: Current Opinion in Biotechnology 9, pp 377-382, 1998).

According to some embodiments, the peptide comprises a fragment of SEQ ID NO: 1. According to other embodiments, the peptide comprises a fragment of an analog of SEQ ID NO: 1. According to certain embodiments, the peptide comprises a fragment of a retro-inverse sequence of: SEQ ID NO: 1 or analog thereof. According to some embodiments, the peptide comprises a peptide fragment consisting of 10 to 23 consecutive amino acids of the parent sequence. In one embodiment, the fragment consists of 11 to 23, 12 to 22, 13 to 21, 14 to 20, 15 to 19, 16 to 18 or 17 such consecutive amino acids. According to another embodiment, the fragment consists of 17 to 23, 18 to 22, or 19 to 21 such consecutive amino acids.

According to some embodiments, the fragment consists of 10 to 23 consecutive amino acids of SEQ ID NO: 1. In one embodiment, the fragment consists of 11 to 23, 12 to 22, 13 to 21, 14 to 20, 15 to 19, 16 to 18 or 17 consecutive amino acids of SEQ ID NO: 1. According to another embodiment, the fragment consists of 17 to 23, 18 to 22, or 19 to 21 consecutive amino acids SEQ ID NO: 1. According to some such embodiments, the fragment comprises the amino acid sequence FLGVLAL (SEQ ID NO: 19). According to some embodiments, the fragment consists of amino acid sequence selected from FLGVLALLGYLAVRPFLPKKKQQ, FLGVLALLGYLAVRPFLPKKKQ, FLGVLALLGYLAVRPFLPKKK, FLGVLALLGYLAVRPFLPKK, FLGVLALLGYLAVRPFLPK, FLGVLALLGYLAVRPFLP, FLGVLALLGYLAVRPFL set forth as SEQ ID NO: 5, 6, 7, 8, 9, 10 and 11, respectively. According to some embodiments, the peptide comprises or consists of said fragment.

According to other embodiments, the fragment consists of 17 to 23 consecutive amino acids of an analog of SEQ ID NO: 1. According to another embodiment, the fragment consists of 18 to 22 or 19 to 21 of consecutive amino acids of the analog of SEQ ID NO: 1. According to such embodiments, the analog is as define in any one of the above embodiments. According to some embodiments, the analog comprises at least one conservative substitution and/or comprises at least one D-amino acid. According to another embodiment, the analog comprises 1 to 3 D-amino acids. According to one embodiment, the analog comprises [10]y, [16]f and [20]k amino acids. According to another embodiment, the analog has the amino acid sequence SEQ ID NO: 2. According to still another embodiment, the fragment consists of 17 to 23, 18 to 22 or 19 to 21 consecutive amino acids of sequence SEQ ID NO: 2. According to a further embodiment, at least 4 amino acids of the analog are D-amino acids. According to one embodiment, all amino acids of the analog are D-amino acids. According to one embodiment, the analog has the amino acid sequence SEQ ID NO: 3. According to still another embodiment, the fragment consists of 17 to 23, 18 to 22 or 19 to 21 consecutive amino acids of sequence SEQ ID NO: 3. According to some embodiments, the fragment consists of an amino acid sequence selected from flgvlallgylavrpflpkkkqq, flgvlallgylavrpflpkkkq, flgvlallgylavrpflpkkk, flgvlallgylavrpflpkk, flgvlallgylavrpflpk flgvlallgylavrpflp, flgvlallgylavrpfl, set forth as SEQ ID NO: 12, 13, 14, 15, 16, 17 and 18, respectively. According to some embodiments, the peptide comprises or consists of said fragments.

According to a further embodiment, the fragment consists of 17 to 23 consecutive amino acids of retro-inverse sequence of SEQ ID NO: 1, i.e. of kqqkkkplfprvalygllalvglf (SEQ ID NO: 4). According to another embodiment, the fragment consists of 18 to 22 or 19 to 21 consecutive amino acids of SEQ ID NO: 4.

As used herein the terms "comprise(s)," "include(s)," "having," "has," "contain(s)," and variants thereof, are intended to be open-ended transitional phrases, terms, or words that do not preclude the possibility of additional acts or structure. The term "comprising" always includes the term "consisting" and when the term "comprising" appears in an embodiment of the disclosure, this same embodiment wherein the term "consisting" replaces the term "comprising" is always also an embodiment of the disclosure. Thus, in certain embodiments, the peptide consists of the amino acid sequence selected from SEQ ID NO: 1, an analog thereof, retro-inverso sequence of SEQ ID NO:1 or of an analog thereof, SEQ ID NO: 4 and a fragment of SEQ ID NO: 1, 2, 3 and 4 or an analog thereof.

In one embodiment, the peptide consists of the sequence SEQ ID NO: 1 (the peptide is referred also as PEP).

According to another embodiment, the peptide consists of an analog of SEQ ID NO: 1. According to some embodiments, the analog is as defined in any one of the above embodiments. According to some embodiments, the analog comprises at least one conservative substitution. According to other embodiments, the analog comprises at least one D-amino acid. According to certain embodiments, the analog comprises at least one conservative substitution and at least one D-amino acid. According to another embodiment, the analog comprises 1 to 3 D-amino acids. According to one embodiment, $^{10}Y$, $^{16}F$, $^{20}K$ are D-amino acid. According to another embodiment, the analog has a sequence SEQ ID NO: 3. According to one embodiment, the peptide consists of the amino acid sequence SEQ ID NO: 2. According to a further embodiment, at least 4 amino acids of the analog are D-amino acids. According to one embodiment, all amino acids of the analog are D-amino acids. According to one embodiment, the analog has the amino acid sequence SEQ ID NO: 3.

According to some embodiments, the peptide consists of a retro-inverse sequence of SEQ ID NO: 1. In such embodiments, the peptide consists of the amino acid sequence SEQ ID NO: 4.

According to some embodiments, the peptide consists of a retro-inverse sequence of the analog of SEQ ID NO: 1. According to some embodiments, the analog is as defined in any one of the above embodiments.

According to other embodiments, the peptide consists of 17 to 23 of consecutive amino acids of an amino acid sequence selected from SEQ ID NO: 1, analog thereof, SEQ ID NO: 2, 3, 4, and retro-inverse sequence of the analog of SEQ ID NO: 1. According to one embodiment, the peptide consists of 17, 18, 19, 20, 21, 22 or 23 consecutive amino acids of SEQ ID NO: 1. According to another embodiment, the peptide consists of 17, 18, 19, 20, 21, 22 or 23 consecutive amino acids of SEQ ID NO: 2. According to such embodiments the peptide comprises the amino acid sequence FLGVLAL (SEQ ID NO: 19).

According to another embodiment, the peptide consists of 17, 18, 19, 20, 21, 22 or 23 consecutive amino acids of SEQ ID NO: 3. According to another embodiment, the peptide consists of 17, 18, 19, 20, 21, 22 or 23 consecutive amino acids of SEQ ID NO: 4.

According to some embodiments, the present invention provides a peptide comprising an amino acid sequence having at least 70% identity to the sequences selected from SEQ ID NO: 1, 2, 3 and 4. According to one embodiment, the peptide comprises an amino acid sequence having at least 75%, at least 80%, at least 85, at least 90%, at least 95%, at least 96%, at least 97% at least 98% or at least 99% identity to the sequences selected from SEQ ID NO: 1, 2, 3 and 4.

According to some embodiments, the present invention provides a peptide consisting of an amino acid sequence selected from: SEQ ID NO: 1, SEQ ID NO: 2, SEQ ID NO: 3 and SEQ ID NO: 4. According to another embodiment, the present invention provides a fragment of such peptide consisting of 17 to 23 amino acids, or an analog of said peptide or said fragment.

According to another aspect, the present invention provides a conjugate of a peptide of the present intention. According to one embodiment, the present invention provides a conjugate of a peptide comprising the amino acid selected from SEQ ID NO: 1, 2, 3, and 4. According to a further embodiment, the present inventions provides a conjugate of a peptide consisting of amino acid sequence selected from SEQ ID NO: 1, 2, 3, and 4. According to a further embodiment, the conjugate is of an peptide comprising an analog of SEQ ID NO: 1. According to another embodiment, the conjugate is of an peptide consisting of an analog of SEQ ID NO: 1. According to one embodiments, the analog comprises the amino acid sequence FLGVLAL (SEQ ID NO: 19).

The term "conjugate" as used herein refers to the association of a peptide with another moiety. According to some embodiments, the moiety is a non-peptidic moiety. According to some embodiment, the peptide is conjugated with polyethylene glycol (PEG), Poly(N-vinylpyrrolidone), polyglycerol, a permeability enhancing moiety and polysaccharides such as glycosyl. According to another embodiment, the peptide is conjugated with a marker. According to some embodiments, the marker is a fluorescent marker such as fluorescein.

The term "permeability-enhancing moiety" refers to any moiety known in the art to facilitate actively or passively or enhance permeability of the compound through body barriers or into the cells. Non-limitative examples of permeability-enhancing moiety include: hydrophobic moieties such as fatty acids, steroids and bulky aromatic or aliphatic compounds; moieties which may have cell-membrane receptors or carriers, such as steroids, vitamins and sugars, natural and non-natural amino acids and transporter peptides, nanoparticles and liposomes.

According to some embodiments, the conjugate comprises the peptide of the present invention and PEG molecule. According to some embodiments, the PEGylation is effected through C-terminus of the peptide. According to other embodiments, the PEGylation is effected through N-terminus of the peptide. According to further embodiments, the PEGylation is effected through a side chain of an amino acid of a peptide.

According to some embodiments, the PEG molecule has molecular weight (Mw) between about 300 daltons to about 100,000 daltons. According to other embodiments, the PEG molecule has a Mw of from about 400 to about 10,000, about 1000 to about 8,000, about 2000 to about 6,000 and about 3,000 to about 5,000 dalton. According to other embodiments, PEG molecule have molecular weight selected from about 10,000 Da to about 20,000 Da, from about 20,000 Da to about 30,000 Da, from about 30,000 Da to about 40,000 Da, from about 40,000 Da to about 50,000 Da, from about 50,000 Da to about 60,000 Da, from about 60,000 Da to about 70,000 Da, and from about 70,000 Da to about 80,000 Da. Non-limiting examples of average molecular weights of the PEG moieties are about 350, about 400 Da, about 600 Da, about 1,000 Da, about 2,000 Da, about 6,000 Da, about 8,000 Da, about 10,000 Da, about 20,000 Da, about 30,000 Da, about 40,000 Da, about 50,000 Da, about 60,000 Da, about 70,000 Da, and about 80,000 Da.

According to some embodiments, the PEG has from 5 to 200 ethylene glycol monomers. According to other embodiments, PEG has from 6 to 150 ethylene glycol monomers. According to other embodiments, PEG has from 8 to 120, from 10 to 100, from 15 to 80 from 20 to 60 or from 30 to 50 ethylene glycol monomers.

According to some embodiments, the present invention provides a conjugate of the peptide comprising or consisting of SEQ ID NO: 1 and PEG. According to some embodiments, the peptide is PEGylated at N-terminus. According to other embodiments, the peptide is PEGylated at C-Terminus. According to some embodiments, the PEG has a molecular weight selected from 300 to 10,000 Da, 350 to 8,000 Da, 400 to 6,000 Da, 1,000 to 4,000 Da or 2,000 Da to 3000 Da. According to other embodiments, the PEG has from 5 to 20 or from 6 to 10 ethylene glycol monomers. According to some embodiments, the present invention provides a conjugate of the peptide comprising or consisting of SEQ ID NO:2 and PEG. According to some embodiments, the peptide is PEGylated at N-Terminus. According to other embodiments, the peptide is PEGylated at C-terminus. According to some embodiments, the PEG has a molecular weight selected from 300 to 10,000 Da, 350 to 8,000 Da, 400 to 6,000 Da, 1,000 to 4,000 Da or 2,000 Da to 3,000 Da. According to other embodiments, the PEG has from 5 to 20 or from 6 to 10 ethylene glycol monomers.

According to some embodiments, the present invention provides a conjugate of the peptide comprising or consisting of SEQ ID NO: 3 or SEQ ID NO: 4 and PEG. According to some embodiments, the peptide is PEGylated at N-Terminus. According to other embodiments, the peptide is PEGylated at C-Terminus. According to some embodiments, the PEG has a molecular weight selected from 300 to 10,000 Da, 350 to 8,000 Da, 400 to 6,000 Da, 1,000 to 4,000 Da or 2,000 Da to 3,000 Da. According to other embodiments, the PEG has from 5 to 20 or from 6 to 10 ethylene glycol monomers.

According to one embodiment, the present invention provides a conjugate of a peptide consisting of amino acid sequence SEQ ID NO: 2 bound through its N-terminus to PEG molecule having between 6 to 10 ethylene glycol monomers. According to another embodiment, the present invention provides a conjugate of a peptide consisting of amino acid sequence SEQ ID NO: 2 bound through its C-terminus to PEG molecule having between 6 to 10 ethylene glycol monomers. According to a further embodiment, the present invention provides a conjugate of a peptide consisting of amino acid sequence SEQ ID NO: 1 bound through its N-terminus to PEG molecule having between 6 to 10 ethylene glycol monomers. According to still another embodiment, the present invention provides a conjugate of a peptide consisting of amino acid sequence SEQ ID NO: 1 bound through its C-terminus to PEG molecule having between 6 to 10 ethylene glycol monomers.

The conjugate of the present invention is profoundly more stable than the parent peptide. According to some embodiment, the half-life of a conjugate of a peptide of the present invention is at least 2 times longer than of the parent peptide. According to some embodiments, the half-life of a conjugate of a peptide of the present invention is at least 3, 5, 8 or 10 times longer than of the parent peptide.

According to another aspect, the present invention provides a pharmaceutical composition comprising at least one peptide or at least one conjugate of the present invention. According to one embodiment, the pharmaceutical composition comprises at least one peptide comprising the amino acid sequence SEQ ID NO: 1. According to another embodiment, the peptide consists of the amino acid sequence SEQ ID NO: 1.

According to another embodiment, the pharmaceutical composition comprises at least one peptide comprising an analog of amino acid sequence SEQ ID NO: 1. According to a further embodiment, the pharmaceutical composition comprises a peptide consisting of an analog of amino acid sequence SEQ ID NO: 1. According to such embodiments, the analog is as defined in any one of the above embodiments. According to some embodiments, the analog comprises the amino acid sequence FLGVLAL (SEQ ID NO: 19). According to some embodiments, the analog comprises at least one conservative substitution and/or comprises at least one D-amino acid. According to another embodiment, the analog comprises 1 to 3 D-amino acids. According to one embodiment, $^{10}$Y, $^{16}$F, $^{20}$K are D-amino acid. According to another embodiment, the analog has the amino acid sequence SEQ ID NO: 2, thus the pharmaceutical composition comprises at least one peptide comprising or consisting of amino acid sequence SEQ ID NO: 2. According to a further embodiment, at least 4 amino acids of the analog are D-amino acids. According to one embodiment, all amino acids of the analog are D-amino acids. According to one embodiment, the analog has the amino acid sequence SEQ ID NO: 3. According to such embodiments, the pharmaceutical composition comprises at least one peptide comprising or consisting of the amino acid sequence SEQ ID NO: 3.

According to some embodiments, the pharmaceutical composition comprises at least one peptide comprising or consisting of the retro-inverse sequence of SEQ ID NO: 1 or of an analog thereof. In one embodiment, the peptide comprises the amino acid sequence SEQ ID NO: 4. In another embodiment, the peptide consists of the amino acid sequence SEQ ID NO: 4.

According to further embodiment, the pharmaceutical composition comprises at least one peptide comprising or consisting of 17 to 23 of consecutive amino acids of the amino acid sequence selected from SEQ ID NO: 1, an analog of SEQ ID NO: 1, SEQ ID NO: 2, SEQ ID NO: 3, SEQ ID NO: 4, and a retro-inverse sequence of the analog of SEQ ID NO: 1. According to some such embodiments, the fragment comprises the amino acid sequence FLGVLAL (SEQ ID NO: 19). According to another embodiment, the pharmaceutical composition comprises at least one peptide comprising an amino acid sequence selected from SEQ ID NOs: 6-18. According to a further embodiment, the pharmaceutical composition comprises at least one peptide consisting of an amino acid sequence selected from SEQ ID NOs: 6-18.

According to a further embodiment, the pharmaceutical composition comprises at least one peptide consisting of an amino acid sequence SEQ ID NO: 1. According to some embodiments, the pharmaceutical composition comprises at least one peptide consisting of an amino acid sequence SEQ ID NO: 2. According to another embodiment, the pharmaceutical composition comprises at least one peptide consisting of an amino acid sequence SEQ ID NO: 3. According to still another embodiment, the pharmaceutical composition comprises at least one peptide consisting of an amino acid sequence SEQ ID NO: 4. According to another embodiment, the pharmaceutical composition comprises at least one fragment of said peptide consisting of 17-23 amino acids of the amino acid sequence selected from SEQ ID NO: 1, 2, 3 and 4.

According to some embodiments, the pharmaceutical composition comprises at least one conjugate of said peptides. According to one embodiment, the conjugate is PEG conjugate. According to certain embodiments, the pharmaceutical composition comprises at least one conjugate of a peptide comprising an amino acid sequence selected from SEQ ID NO: 1, 2, 3 and 4, and PEG. According to other embodiments, the pharmaceutical composition comprises at least one conjugate of a peptide consisting of an amino acid sequence selected from SEQ ID NO: 1, 2, 3 and 4, and PEG. According to some embodiments, the peptide is PEGylated at N-terminus. According to other embodiments, the peptide is PEGylated at C-terminus. According to some embodiments, the PEG has a molecular weight selected from 300 to 10,000 Da, 350 to 8,000 Da, 400 to 6,000 Da, 1,000 to 4,000 Da or 2,000 Da to 3,000 Da. According to some embodiments, the PEG has a molecular weight selected from 300 to 1,000 Da.

According to some embodiments, the pharmaceutical composition comprises at least one conjugate comprising the peptide comprising amino acid sequence SEQ ID NO: 2 and PEG having from 5 to 15 ethylene glycol monomers, such as 8 monomers, bound to the C-terminus or to the N-terminus of the peptide. According to another embodiment, the pharmaceutical composition comprises at least one conjugate consisting of the peptide comprising amino acid sequence SEQ ID NO: 2 and PEG having from 5 to 15 ethylene glycol monomers, such as 8 monomers, bound to the C-terminus or to the N-terminus of the peptide.

The terms "pharmaceutical composition" and "pharmaceutically acceptable composition" are used herein interchangeably and refer to a composition comprising the peptide of the present invention or a conjugate thereof, formulated together with one or more pharmaceutically acceptable carriers.

The terms "pharmaceutically acceptable carrier" or "pharmaceutically acceptable excipient" as used herein refer to any and all solvents, dispersion media, preservatives, antioxidants, coatings, isotonic and absorption delaying agents, surfactants, fillers, disintegrants, binders, diluents, lubricants, glidants, pH adjusting agents, buffering agents, enhancers, wetting agents, solubilizing agents, surfactants, antioxidants the like, that are compatible with pharmaceutical administration. The use of such media and agents for pharmaceutically active substances is well known in the art. The compositions may contain other active agents providing supplemental, additional, or enhanced therapeutic functions.

According to any one of the above embodiments, the pharmaceutical composition of the present invention may be administered by any known route of administration. The term "administering" or "administration of" a substance, a compound, an agent or a pharmaceutical composition to a subject can be carried out using one of a variety of methods known to those skilled in the art. For example, a compound, an agent or a composition can be administered enterally or parenterally. Enterally refers to administration via the gastrointestinal tract including per os, sublingually or rectally. Parenteral administration includes administration intravenously, intradermally, intramuscularly, intraperitoneally, subcutaneously, ocularly, sublingually, intranasally, by inhalation, intraspinally, intracerebrally, and transdermally. A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

In one embodiment, the pharmaceutical composition comprising the peptide or the conjugate of the present invention is administered via a systemic administration. For example, the pharmaceutical composition comprising the peptide or the conjugated of the present invention is administered orally, intravenously or transdermally. Alternatively, the composition is administered intramuscularly, intraperitoneally, subcutaneously, ocularly, sublingually, or intranasally.

The pharmaceutical composition according the present invention may be prepared in any known method. In particular, the pharmaceutical composition may be formulated using a method known in the art so as to provide rapid, continuous or delayed release of the active ingredient after administration. In one particular embodiment, the pharmaceutical composition is formulated as a solid dosage form selected from tablets, capsules, powder or granules. In another embodiment, the pharmaceutical composition is formulated as a liquid or semi-liquid dosage form selected from an elixir, tincture, suspension, syrup, emulsion or gel.

Pharmaceutical compositions intended for oral use may be prepared according to any method known to the art for the manufacture of pharmaceutical compositions and may further comprise one or more agents selected from sweetening agents, flavoring agents, coloring agents and preserving agents in order to provide pharmaceutically elegant and palatable preparations. Tablets contain the active agent in admixture with non-toxic pharmaceutically acceptable excipients, which are suitable for the manufacture of tablets. These excipients may be, e.g., inert diluents such as calcium carbonate, sodium carbonate, lactose, calcium phosphate, or sodium phosphate; granulating and disintegrating agents, e.g., corn starch or alginic acid; binders; and lubricating agents. The tablets are optionally coated utilizing known techniques to delay disintegration and absorption in the gastrointestinal tract and thereby provide an extended release of the drug over a longer period.

According to one aspect, the pharmaceutical composition, according to any one of the above embodiments, is for use in treating cancer. According to some more specific embodiments, the pharmaceutical composition comprises at least one peptide consisting of an amino acid sequence selected from SEQ ID NOs: 1-4 a fragment thereof consisting of 17-23 amino acids, or an analog of said peptide or said fragment. According to other embodiments, the pharmaceutical composition for use comprises a conjugate of such peptides, e.g. PEG conjugate.

The term "treating" as used herein refers to taking steps to obtain beneficial or desired results, including clinical results. Beneficial or desired clinical results include, but are not limited to, alleviation or amelioration of one or more symptoms or parameters associated with cancer, delay or slowing of that impairment, amelioration, palliation or stabilization of that impairment, and other beneficial results.

According to some embodiments, the cancer is associated with enhanced or increased expression of NAF-1 protein. The terms "NAF-1" and "CISD2" refer to a protein, wherein the human protein has Gene ID: 493856.

According to any one of the above embodiments, the cancer is selected from breast, prostate, gastric, cervical, liver, pancreas, head, neck, and laryngeal cancer.

According to other embodiments, the composition is for use in treating cancer selected from mammary carcinomas, melanoma, skin neoplasms, lymphoma, leukemia, gastrointestinal tumors, including colon carcinomas, stomach carcinomas, pancreas carcinomas, colon cancer, small intestine cancer, ovarial carcinomas, cervical carcinomas, lung cancer, prostate cancer, kidney cell carcinomas and/or liver metastases.

According to any one of the above embodiments, the pharmaceutical composition may be administered in combination with another anti-cancer therapy such as immunomodulators, activated lymphocytes, lymphocyte activating agent, kinase inhibitor, chemotherapeutic agent or any other anti-cancer agent.

According to another aspect, the present invention provides a method of treating cancer in a subject in need thereof comprising administering the peptide, the conjugate or the pharmaceutical composition of the present invention to said subject. According to one embodiment, the pharmaceutical composition comprises an effective amount of the peptides or the conjugates according to the present invention. According to some specific embodiments, the method comprises administering a pharmaceutical composition comprising an effective amount of the peptide comprising an amino acid sequence selected SEQ ID NO: 1-18 or conjugates thereof. According to other specific embodiments, the method comprises administering a pharmaceutical composition comprising an effective amount of the peptide consisting of an amino acid sequence selected SEQ ID NO: 1-18 or conjugates thereof. According to some embodiments, the method comprises administering a pharmaceutical composition comprising an effective amount of the peptide comprising or consisting of an amino acid sequence selected SEQ ID NO: 1, 2, 3 and 4, a fragment thereof consisting of 17-23 amino acids, or an analog of said peptide or said fragment. According to one embodiment, the pharmaceutical composition comprises the conjugates of the present invention. According to some embodiments, the method comprises administering the pharmaceutical composition of the present invention in combination with another anti-cancer therapy, as described above.

As used herein, the term "about", when referring to a measurable value such as an amount, a temporal duration, and the like, is meant to encompass variations of +/−10%, or +/−5%, +/−1%, or even +/−0.1% from the specified value.

Having now generally described the invention, the same will be more readily understood through reference to the following examples, which are provided by way of illustration and are not intended to be limiting of the present invention.

EXAMPLES

Example 1. PEP-FL Selectively Penetrates into Cancer Breast Cells

The peptide having the amino acid sequence FLGV-LALLGYLAVRPFLPKKKQQK (SEQ ID NO: 1, also referred to as PEP), corresponding to amino acids 44-67 of human NAF-1 is part of the transmembranal domain and the adjacent cytoplasmic region of human NAF-1 (FIG. 1). This region of the protein is not involved in the coordination of the 2Fe-2S cluster of NAF-1.

Figure 2:
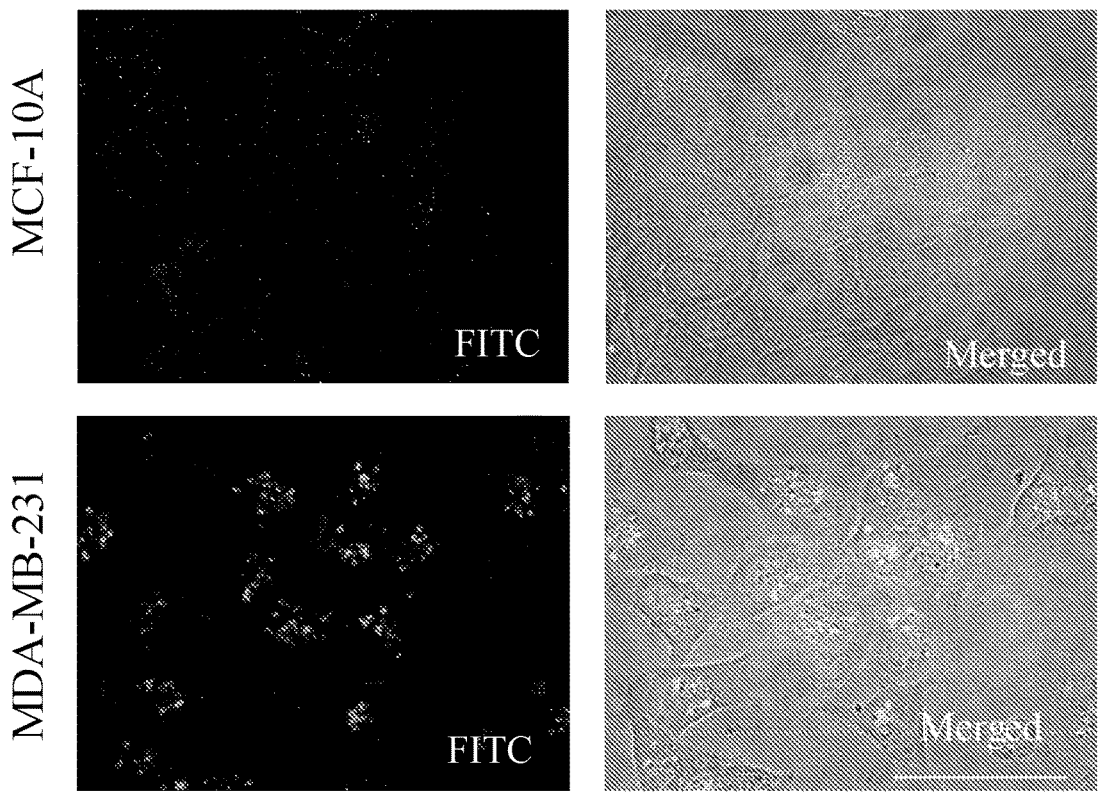
FIG. 2 shows penetration of a fluorescein-labeled peptide of SEQ ID NO: 1 (PEP-FL) into human epithelial breast cancer cells (MDA-MB-231) or non-malignant MCF-10A cells. Nuclei were stained with Hoechst 33342 and mitochondria with the rhodamine derivate RPA.
Figure 3:
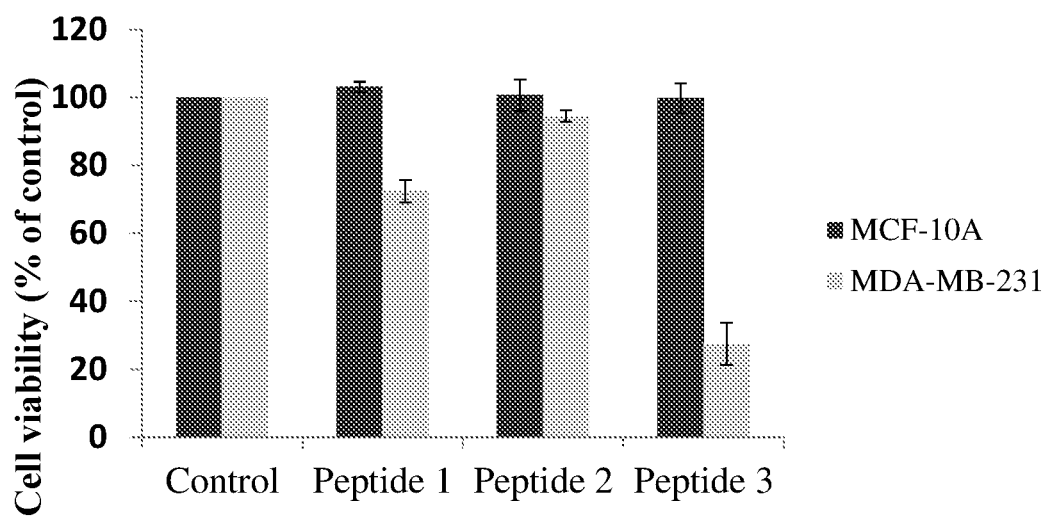
FIG. 3 shows the effect of different NAF-1-derived peptides on the viability of non-malignant MCF-10A cells (dark bars) or malignant MDA-MB-231 cells (gray bars). Peptide 1—residues 80-94 of NAF-1, Peptide 2—non relevant peptide, Peptide 3—residues 44-67 of NAF-1 (SEQ ID NO: 1), control—no peptide added.

The ability of the peptide having the sequence SEQ ID NO: 1 to penetrate into the cells and its effect on cells' viability was tested as following. Green fluorescein was conjugated to the peptide having SEQ ID NO: 1 (the labeled peptide is referred as PEP-FL). Then, the fluorescent peptide was incubated with normal, non-tumor epithelial cell line (MCF-10A) and malignant (MDA-MB-231) breast epithelial cells. The mitochondria of the cells were labeled red with RPA and the cells' nuclei were labeled with Hoechst 33342 (blue dye). As indicated in FIG. 2, the fluorescent peptide was preferentially up-taken by the cancer MDA-MB-231 cells, but not by normal cells (FIG. 2, lower panels, bright spots). Furthermore, malignant breast cells (right bars on FIG. 3: were killed by the peptides having SEQ ID NO:1 whereas the normal cells (left bars in FIG. 3) were not affected (in FIG. 3B: Peptide 3—peptide having SEQ ID NO: 1; Peptide 1—residues 80-94 of NAF-1—region interacting with thioredoxin).

Example 2. Efficacy of the Peptide SEQ ID NO: 1 in Killing of Breast Cancer Cells In order to validate the cell-based results, the efficacy of peptide having SEQ ID NO:1 the peptide was studied in "a tumor like" 3D cancer cell spheroids of MDA-MB-231 cells.

The MDA-MB-231 cells were plated in quadruplicate at $2 \times 10^3$ cells per well in a 96 well ULA plate (Corning 7007) and the cells were further cultured for 3 days to form spheroids. Then, the spheroids were treated with the peptides having SEQ ID NO:1 and the apoptosis of spheroids was assayed using Annexin V-red detection marker. Spheroids were imaged at ×10 magnification in an IncuCyte Zoom Live-cell analysis system (Essen Bioscience) at 37° C. with 5% $CO_2$. Spheroid cell images were recorded every two hours and the resulting red colors, reflecting cell apoptosis, were analyzed with the IncuCyte software.)

Figure 4:
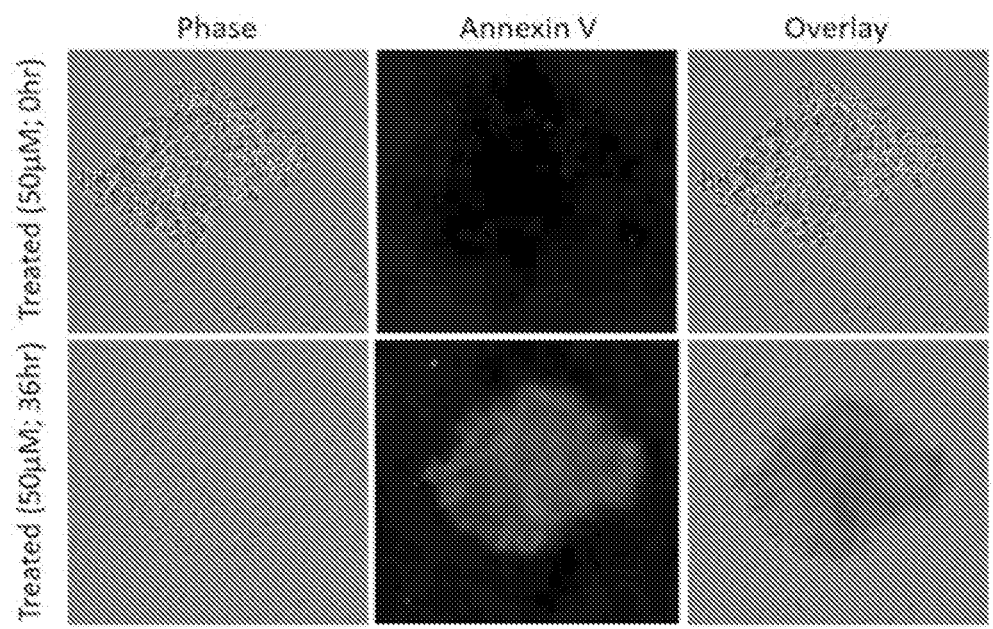
FIG. 4 shows activation of apoptosis in cancer, MDA-MB-231 breast cancer spheroids were treated with 50 µM of peptide of SEQ ID NO: 1 for 36 hours. The apoptosis was visualized using Annexin V detection marker. Imaging was performed with IncuCyte™ (Essen BioScience).

FIG. 4 clearly shows that after a 36 hours incubation of the peptide (FIG. 4, lower panels) with the 3D spheroids of the breast cancer MDA-MB-231 cells, all tumor-like cells were killed. The death of cells MDA-MB-231 cells in the presence of the peptide having SEQ ID NO: 1 was observed on phase images as well as on the images from the confocal microscope detecting the fluorescence obtained from Annexin V-red marker.

Example 3. The D-PEP is Efficient in an Animal Model Systems of Breast Cancer

An analog of the peptide of SEQ ID NO:1 in which all amino acids were substituted to D-amino acids was synthetized. The analog had the amino acid sequence flgvlallgy-lavrpflpkkkqqk (SEQ ID NO: 3, referred also as D-PEP).

Figure 5:
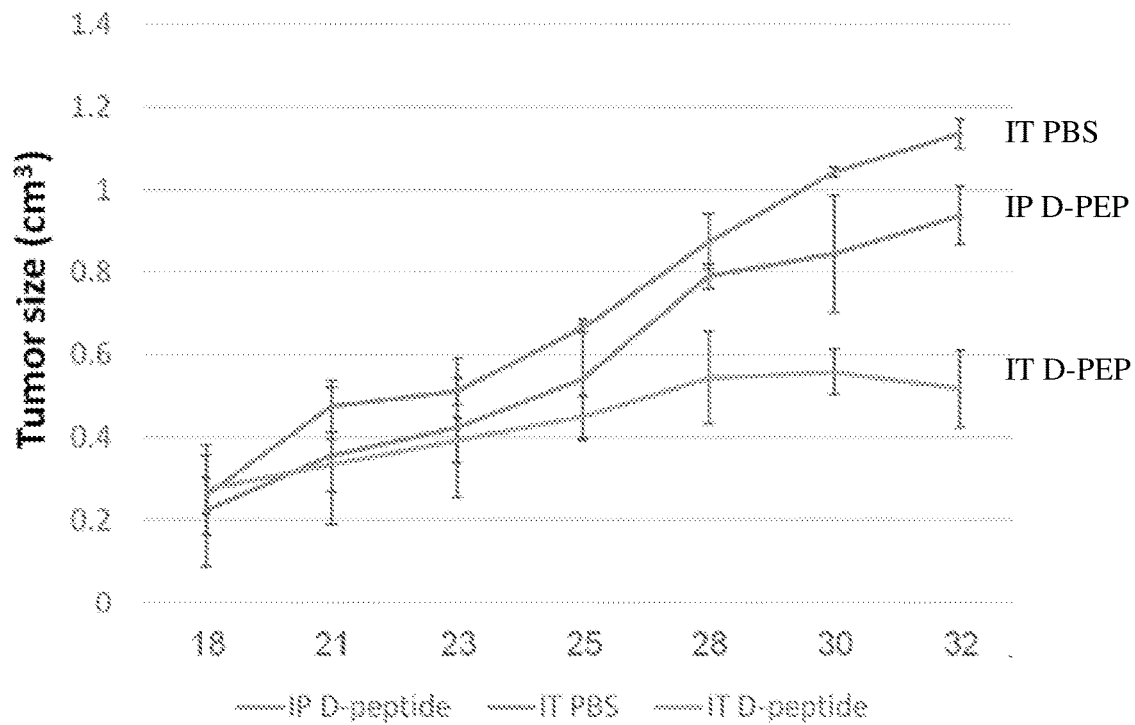
FIG. 5 shows the effect of the injection of the D-peptide having SEQ ID NO: 3 (D-PEP) on the size of a tumor which was developed in 5-6 weeks old mice following injection of MDA-MB-231 breast cancer cells. The peptide (100 µl, 10 µM) was injected intraperitoneal (IP D-PEP), or intratumoral (IT D-PEP), and the effect was compared to control mice, injected with 100 µl PBS (IT PBS).

30 female athymic nude (FOXN1NU) mice (5-6 weeks old) were injected subcutaneously (S.C.) with $2.5 \times 10^6$ MDA-MB-231 cells overexpressing NAF-1. Two and half weeks (day 18) after S.C. injection, mice weight and tumor size was measured. Mice were divided into three different treatment groups that were administrated 3 serial injections per week, on days 18, 21, 23, 25, 28, and 30. The groups were as follows: Group 1: Intraperitoneal (IP) injection of 135 µg/Kg D-PEP; Group 2: Intratumoral (IT) injection of PBS—control; and Group 3: Intratumoral (IT) injection of 135 µg/Kg D-PEP. On days 18, 21, 23, 25, 28 and 30 after S.C. injection of the tumor cells, tumor size and mice weight was measured in all groups. There was not significant change in the weight of mice in all groups suggesting that the peptide was not toxic. The results showing the change in mean tumor size over time as a function of different treatments are presented in FIG. 5. As can be seen from FIG. 5, Group 3 treated mice (IT injected peptide) developed the smallest tumors.

Example 4. Cite of Action of PEP within the Cells

Figure 6A:
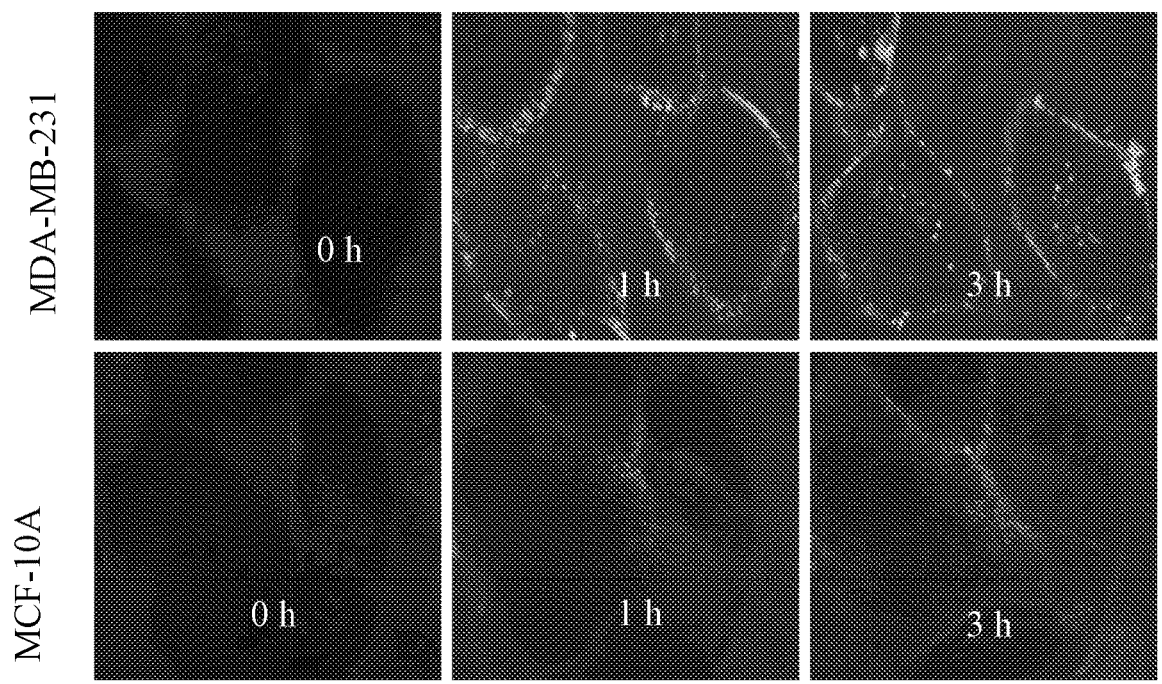
FIG. 6A: confocal images of PEP-FL peptide at indicated time points.
Figure 6B:
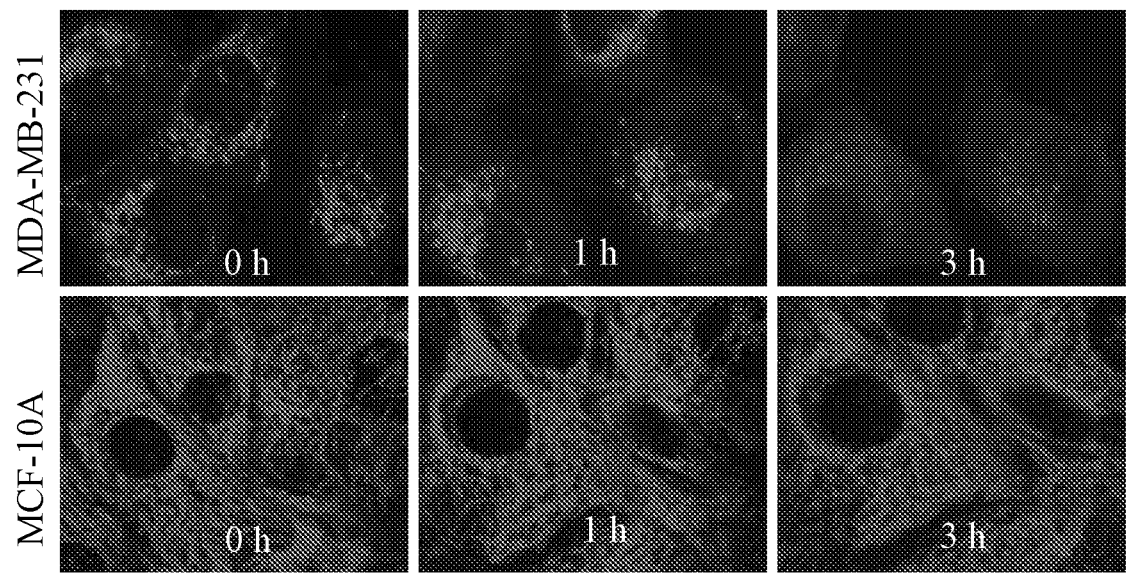
FIG. 6B: confocal images of rhodamine (Rh) 800 labeled mitochondria of MDA-MB-231 and MCF-10A cells.
Figure 6C:
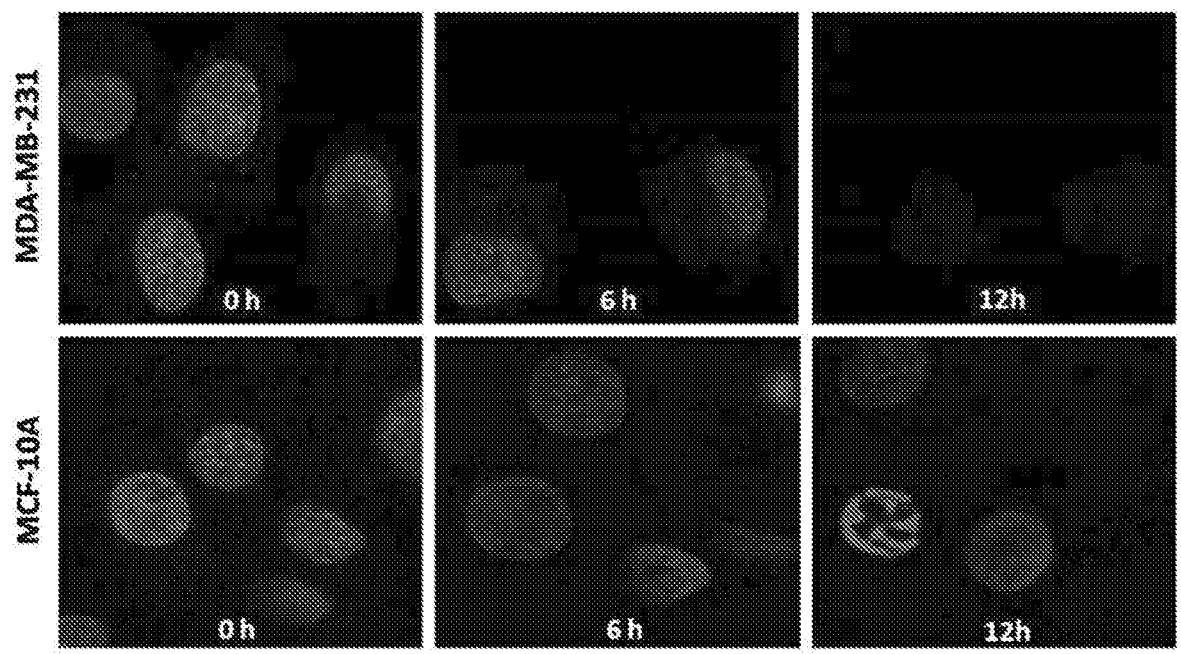
FIG. 6C—confocal images of Hoechst 33342 stained nuclei.

To elucidate the site of action of the peptide having SEQ ID NO: 1, the peptide was labeled as described in Example 1 and incubated with normal and malignant cells (MCF-10A and MDA-MB-231 cells, respectively). As can be seen from FIG. 6A, the fluorescently marked peptide was preferentially up-taken by the cancer cells (MDA-MB-231: upper panel). In an initial assessment of the organelles that were affected by the PEP-FL, it was found that the malignant cells' mitochondria marked in red and shown as bright pattern in the figure (FIG. 6B), disappeared within three hours after the peptide addition to the cells. In addition, it can be seen from FIG. 6C, that while no serious damage was caused to the nuclei (marked blue—bright spheroid shapes in the figure) of normal (MCF-10A—lower panel) cells, after 12 hours of incubation of malignant (MDA-MB-231) cells with the PEP-FL, the nuclei of these cell completely disappeared. Without being bound to any specific theory it was estimates that the peptide affects or disrupts the structure of the mitochondrial and nuclear membrane.

Example 5. Effect of D-PEP on PC3 and MDA-MB-231 Spheroids

Similarly to Example 2, the effect of D-PEP on "tumor like" 3D cancer cell spheroids of prostate cancer cells PC3 and MDA-MB-231, was tested and quantified. Annexin V-red apoptosis marker indicator was used to assess cytotoxicity and the cytotoxicity was calculated as integrated intensity over the surface (RCU×µm²/Image).

Figure 7:
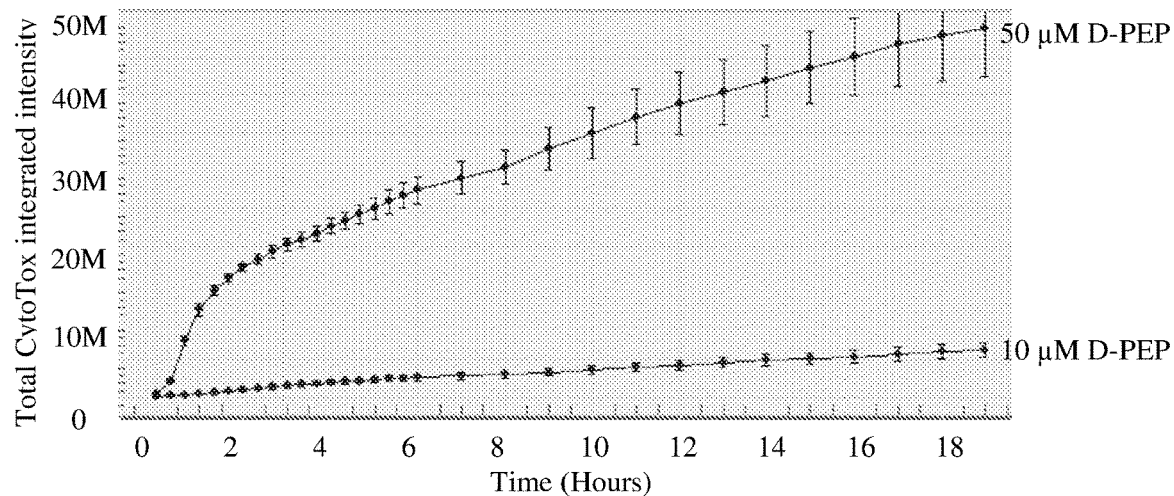
FIG. 7 shows total toxicity integrated intensity (RCU× µm$^2$/Image) calculated for PC3 (prostate cancer) spheroids treated with 10 or 50 µM of D-PEP for 18 hours.
Figure 8:
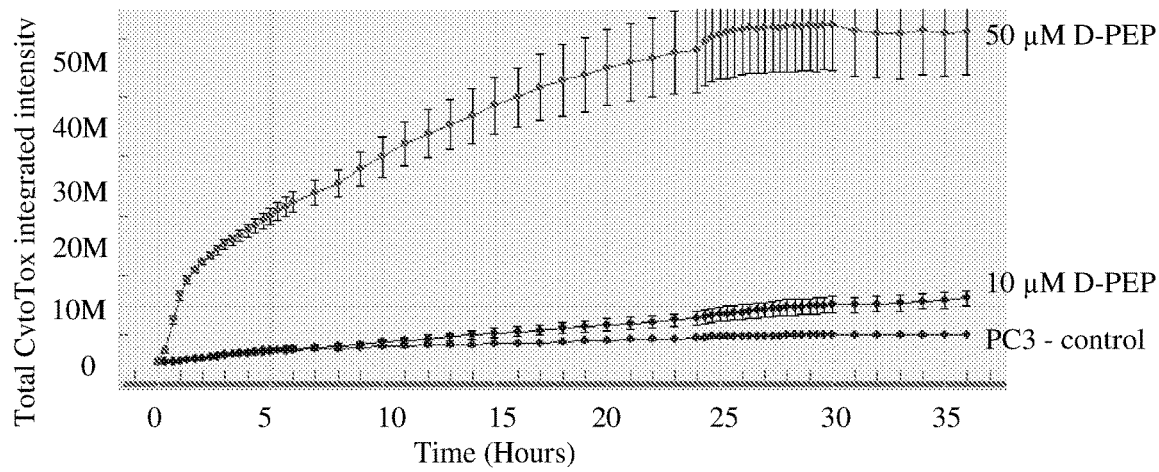
FIG. 8 shows total toxicity integrated intensity calculated for PC3 spheroids treated with 10 or 50 µM of D-PEP for 36 hours.

As follows from FIG. 7, 50 µM of D-PEP (SEQ ID NO: 3) after incubation for 8 hours with PC3 spheroids showed substantial cytotoxic effect, whereas for 10 µM of D-PEP, the obtained effect was much more moderate. Similarly, the effect of 50 µM of D-PEP when incubated for 36 hour with PC3 spheroids provided much more significant cytotoxic effect than 10 µM of D-PEP when compared to the control (FIG. 8).

Figure 9:
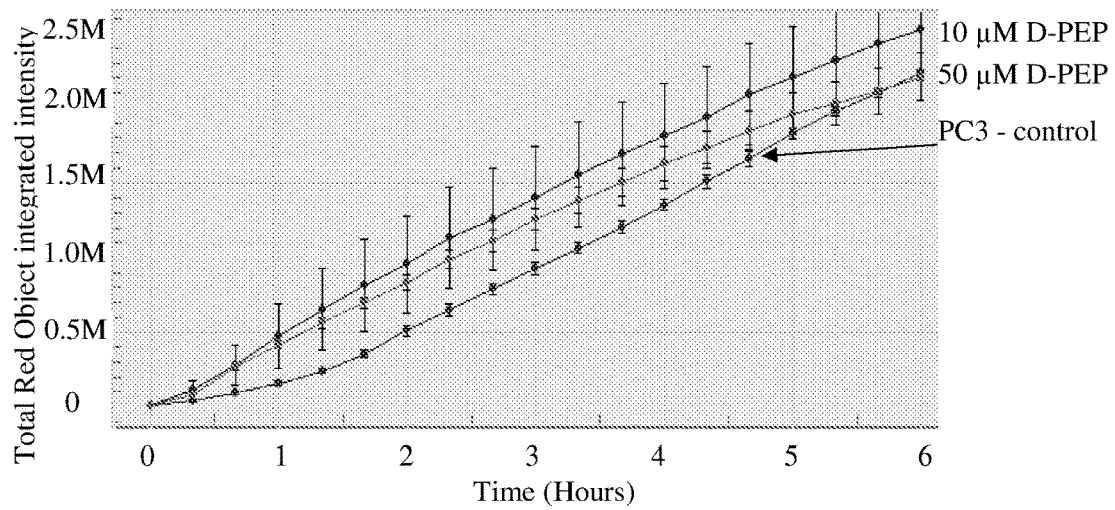
FIG. 9 shows total ROS integrated intensity calculated for PC3 spheroids treated with 10 or 50 µM of D-PEP for 6 hours.

The effect of D-PEP on appearance of reactive oxygen species (ROS) was estimated using fluorogenic probe Cell-ROS® Deep Red Reagent. As follows from FIG. 9, 50 µM of D-PEP efficiently increased the oxidative stress of the PC3 spheroids. 10 µM of D-PEP also increased the oxidative stress, though less efficiently than 50 µM dose. However, the difference in oxidative stress between 10 µM and the control diminish after about 5.5 hours.

Figure 10:
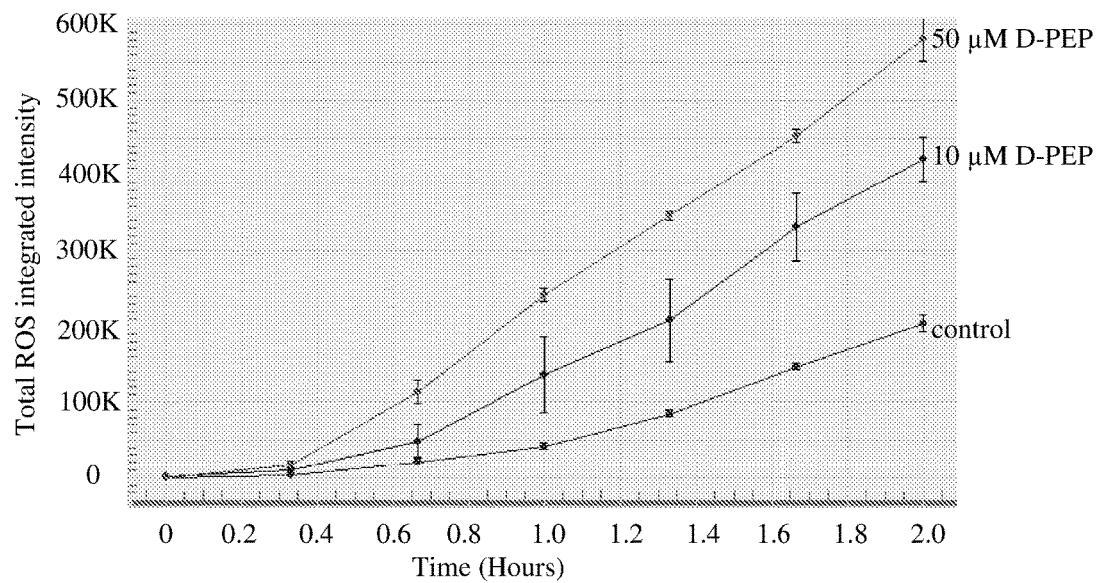
FIG. 10 shows the total ROS integrated intensity calculated for MDA-MB-231 breast cancer spheroids treated with 10 or 50 µM of D-PEP for 6 hours.
Figure 11:
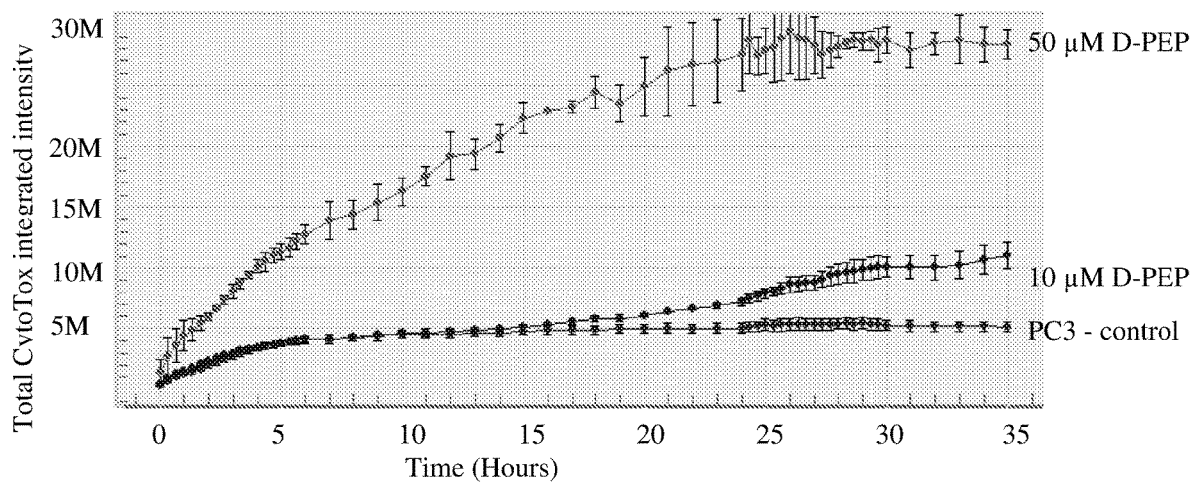
FIG. 11 shows a total toxicity integrated intensity calculated for MDA-MB-231 breast cancer spheroids treated with 10 or 50 µM of D-PEP for 36 hours.

Appearance of ROS in the presence of D-PEP tested also using MDA-MB-231 (also denoted as MDA231). It can be seen from FIG. 10 a significant difference in appearance of ROS for both doses, 10 and 50 µM versus the control, while 50 µM demonstrated a profound difference in comparison to 10 µM. The cytotoxicity of D-PEP incubated for 36 hours with MDA-MB-231 cells was measured as well. As can be seen from FIG. 11, the cytotoxicity was comparable to that seen for PC3 cell.

From these experiments it clearly follows that the peptide having SEQ ID NO: 1 and its D-analog having SEQ ID NO: 3 can efficiently eliminate cancer cells. Without wishing to be bound by any theory or mechanism of action it is proposed that partially this may be attributed to the increased oxidative stress caused by that peptide.

Example 6. Alanine Scan

A preliminary alanine scan was performed for the peptide having SEQ ID NO:1, substituting each time 2 amino acids by alanine residues. As follows from the results of the alanine scan, some of the amino acids may be substituted for alanine without any significant change in the structure of these peptides in DPC as shown in CD analysis (data not shown).

Figure 18A:
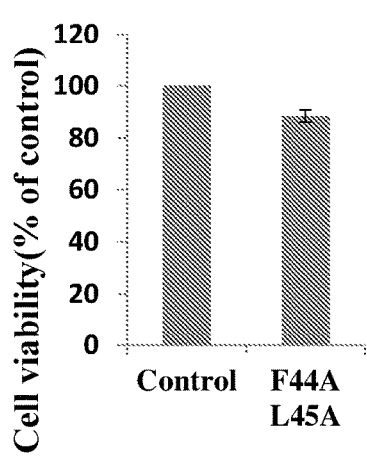
FIG. 18. Shows the effect of 3 different analogs: F44A-L45A-PEP (FIG. 18A), L48A-L50A-PEP (FIG. 18B) and F44A-L45A-L48-PEP (FIG. 18C) on the viability of malignant MDA-MB-231 cells.
Figure 18B:
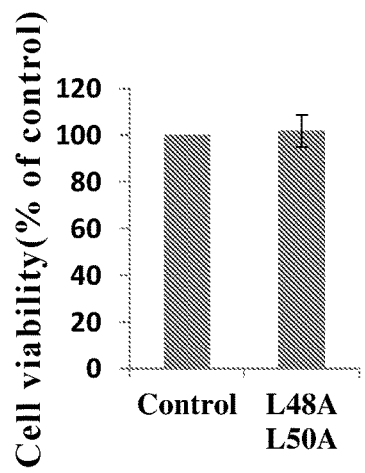
Figure 18C:
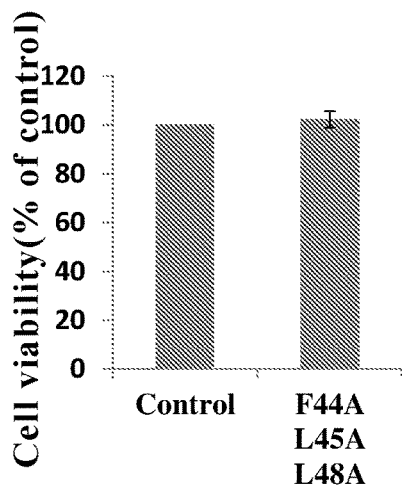

However, substitution of several amino acids to Ala drastically diminished the toxicity of these analogs. For example, analog PEP-F44A-L45A having the sequence AAGVLALLGYLAVRPFLPKKKQQK as set forth in SEQ ID NO: 20, analog PEP-L48A-L50A having the sequence FLGVAAALGYLAVRPFLPKKKQQK as set forth in SEQ ID NO: 22, and PEP-F44A-L45A-L48A having the sequence AAGVAALLGYLAVRPFLPKKKQQK as set forth in SEQ ID NO: 21 completely lost their cytotoxic activity, as can be seen in FIG. 18.

Example 7. D-Peptides

Figure 12:
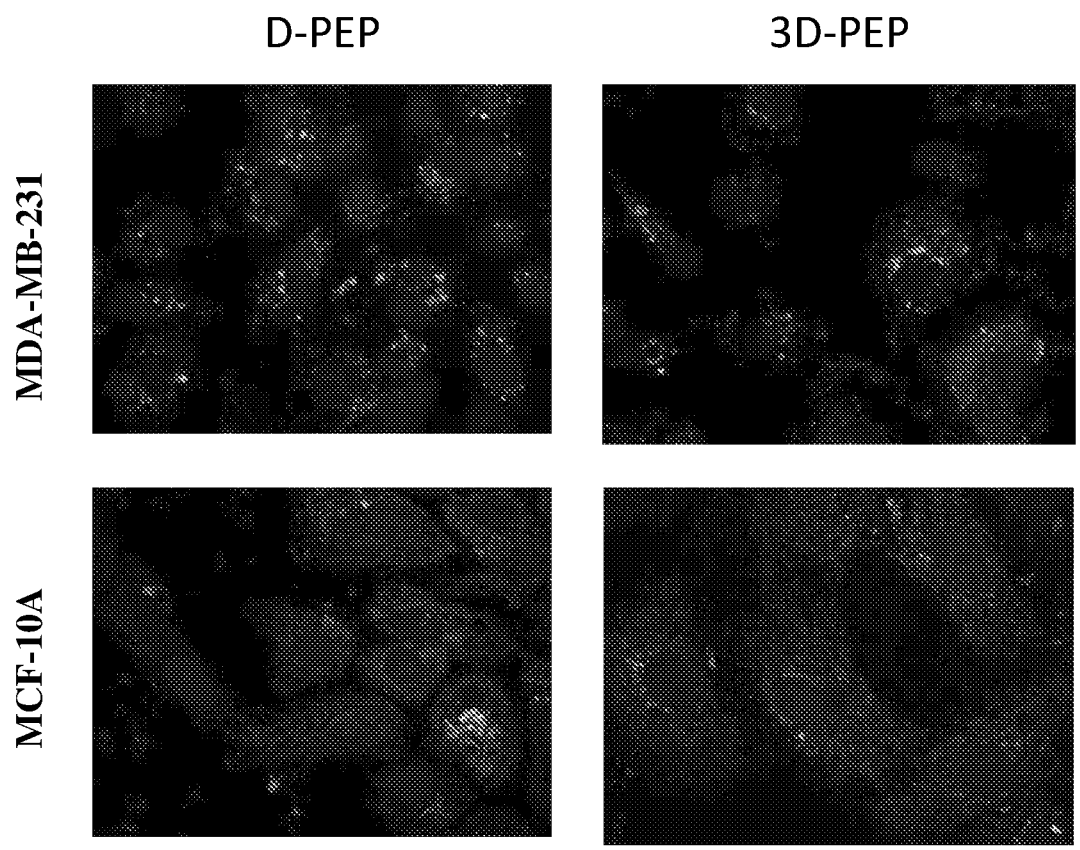
FIG. 12 shows the penetration of the fluorescein-labeled peptides SEQ ID NO: 3 (D-PEP-FL) and SEQ ID NO: 2 (3D-PEP-FL) peptides into malignant cells MDA-MB-231 (upper panel) or non-malignant MCF-10A cells (lower panel). Nuclei were stained with Hoechst 33342 and mitochondria with RPA. The bright spots on the figure show the florescence obtained from fluorescein.

In addition to D-PEP peptide (SEQ ID NO:3), in which all amino acids of SEQ ID NO: 1 were substituted to D-amino acids, a peptide comprising only 3 D-amino acids was produced and has the sequence FLGVLALLGyLAVRP-fLPKkKQQK (SEQ ID NO: 2, referred as 3D-PEP). This peptide, as well as D-PEP, both marked with Fluorescein, were tested for their ability to penetrate into non-tumor MCF-10A and malignant MDA-MB-231 and for their toxicity, as described in Example 3. Briefly, cells were incubated with 10 µM of each sample of the peptides for 3 h and then intensively washed. Cell fluorescence was observed by semi-confocal microscope. For cell viability measurement, cells were incubated with 10 µM or 5 µM of each one of the peptides for 5 days and then cell viability was assayed using Alamar blue assay. It was shown that while the penetration of these two D-peptides to MCF-10A cells was very limited, they were clearly visualized within the malignant MDA-MB-231 cells (FIG. 12). Both peptides showed high toxicity to MDA-MB-231 cells.

Example 8. Toxicity of 3D-PEP

Figure 13:
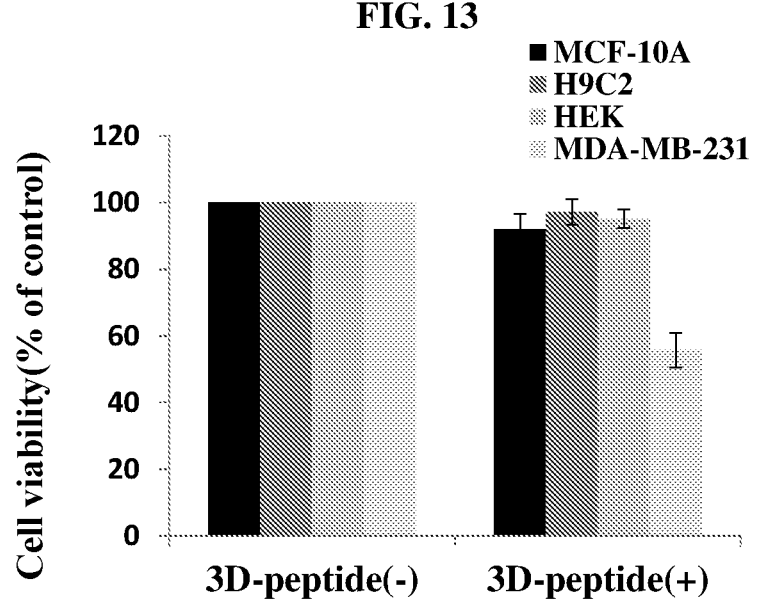
FIG. 13 shows the effect of D-PEP or 3D-PEP on viability of MCF-10A, H9C2, HEK and MDA-MB-231 cells.

A toxicity of 3D-PEP (SEQ ID NO: 2) was tested in normal cells (MCF-10A, H9C2 and HEK) and in malignant cells MDA-MB-231. Briefly, cells were planted in 96 well plate one day before the experiment at the next day cells were incubated with 25 µM of 3D-PEP peptides or with negative control for 2 days. After 2 days of incubation, cells were washed and their viability was assayed using presto blue (Invitrogen) assay. The results are presented in FIG. 13. It can be clearly seen that the peptide 3D-PEP (SEQ ID NO: 2) reduced the vitality of the malignant cells to about 55% and did not have any significant effect on the healthy cells.

Example 9. Structural Characteristics of Peptides Having SEQ ID NO: 1, 2 and 3

Figure 14A:
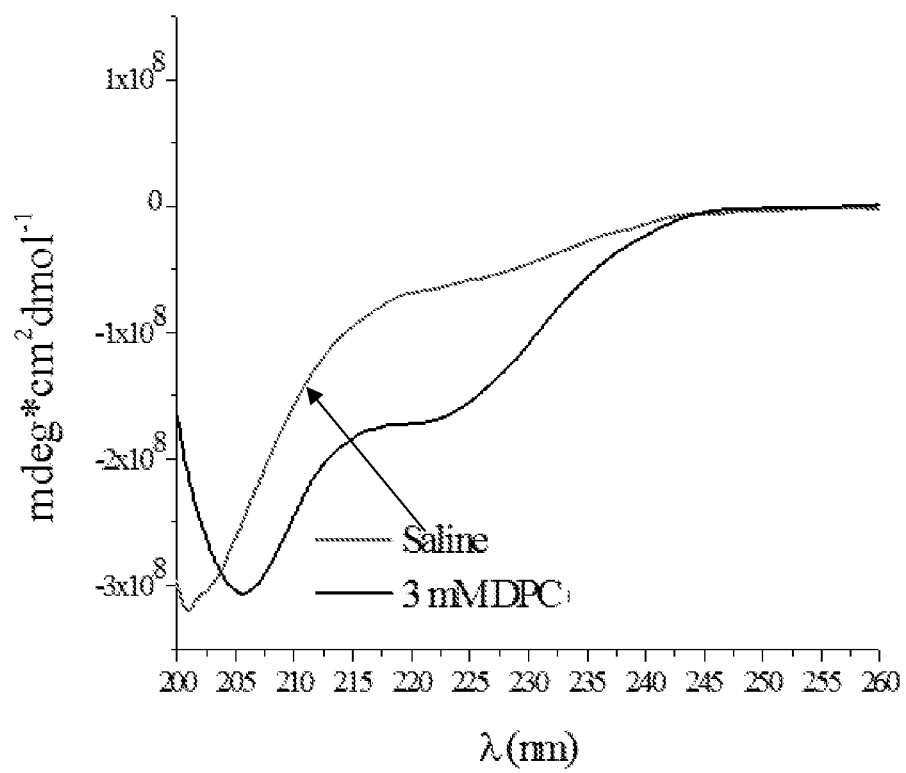
FIG. 14 shows circular dichroism (CD) of the peptide of SEQ ID NO: 1 in saline and in 3 mM dodecylphosphocholine (DPC, FIG. 14A) and CD of 3D-PEP (FIG. 14B) and D-PEP (FIG. 14C) in 3 mM of DPC.
Figure 14B:
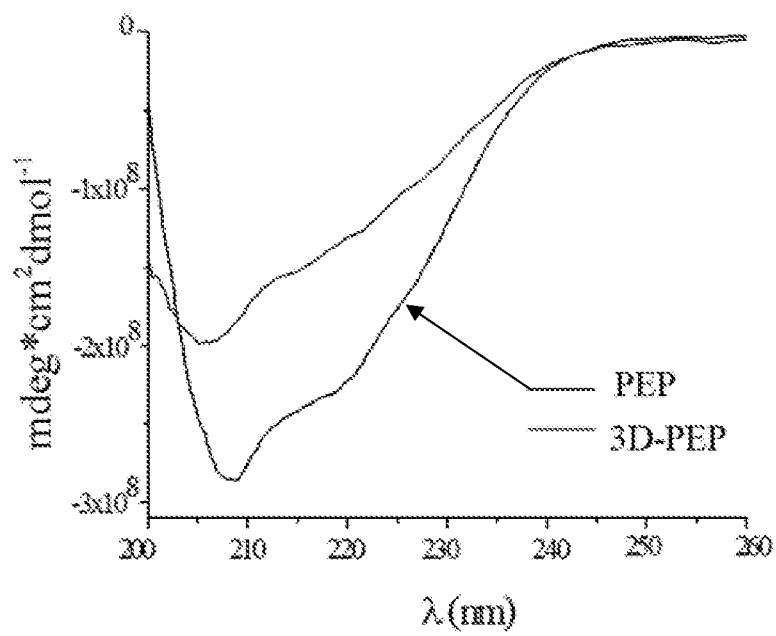
Figure 14C:
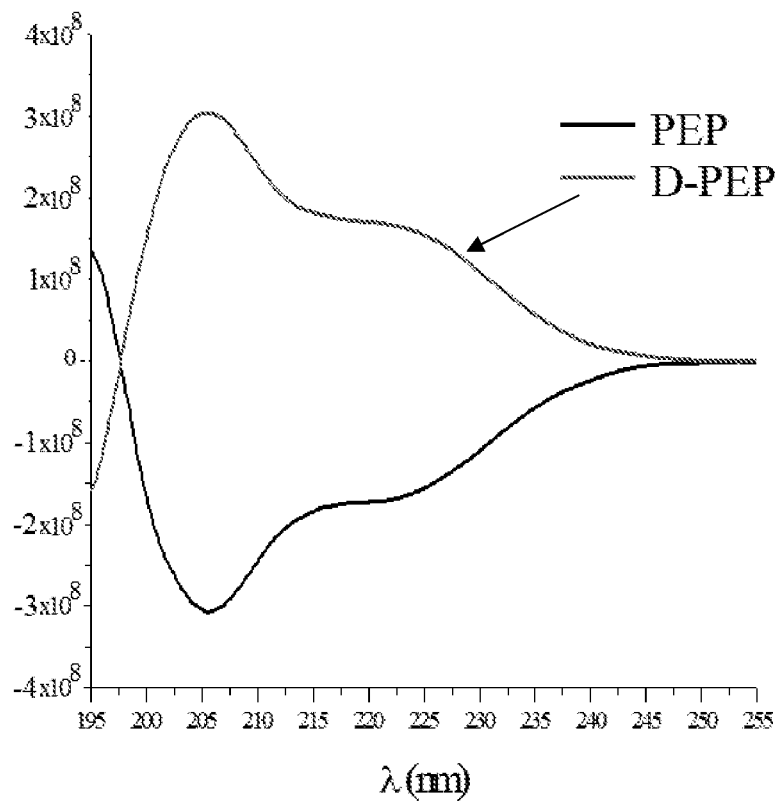

The peptide having SEQ ID NO: 1 is derived from part of NAF-1 transmembrane helix and outer membrane flexible loop. Circular dichroism (CD) spectrum of the peptide in saline showed no specific structure. In the presence of 3 mM Dodecylphosphocholine (DPC) that forms micelles (demonstrate the membrane), the CD spectrum of the peptide showed the peptide had mostly helical structure and some disordered features (see FIG. 14A). 3D-PEP (SEQ ID NO: 2) and D-PEP (SEQ ID NO: 3) showed similar picture (FIG. 14 B-C).

Example 10. PEGylating of 3D-PEP Peptide

3D-PEP peptides were PEGylated in their N- or C-termini using Fmoc-N-amido-PEG8-acid. For N-terminus PEGylation, 450 mg of 3D-PEP, synthesized on resin and previously N terminus de-protected, were swollen for 40 min in 10 ml of DMF. Then 123.5 mg HATU, 245 mg PEG and 135 µl DIEA were mixed on ice for 4 min and were added to the peptide for 60 min for PEG coupling. The peptide was washed five times with 10 ml DMF and then was Fmoc de-protected using 8 ml 20% piperidine in DMF for 10 min twice. For C terminus PEGylation 458 mg rink amid resin was swollen for 40 min in 10 ml of DMF. The Resin was Fmoc de-protected as described and washed five times with 10 ml of DMF. The PEG was coupled to the resin as describe above for 35 min. After the PEGylated resin was washed the remaining free amines on the resin was capped for 10 min using 2 ml acetic anhydride and 4 ml pyridine mixed with 4 ml DMF. The PEGylated resin was washed and de-protected as described above and was placed in the peptide synthesizer for the peptide synthesis.

The resulted N-terminus PEGylated 3D-PEP (referred as PEG-N-3D-PEP) and C-terminus PEGylated 3D-PEP (referred as PEG-C-3D-PEP) have the formula I and II, respectively.

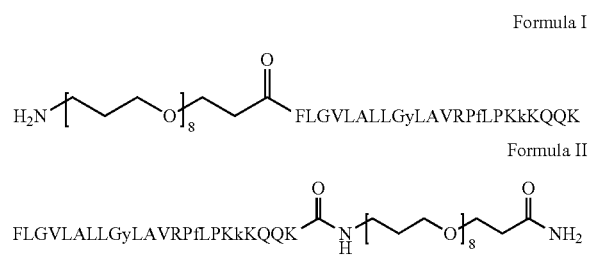

Formula I

Formula II

Figure 15A:
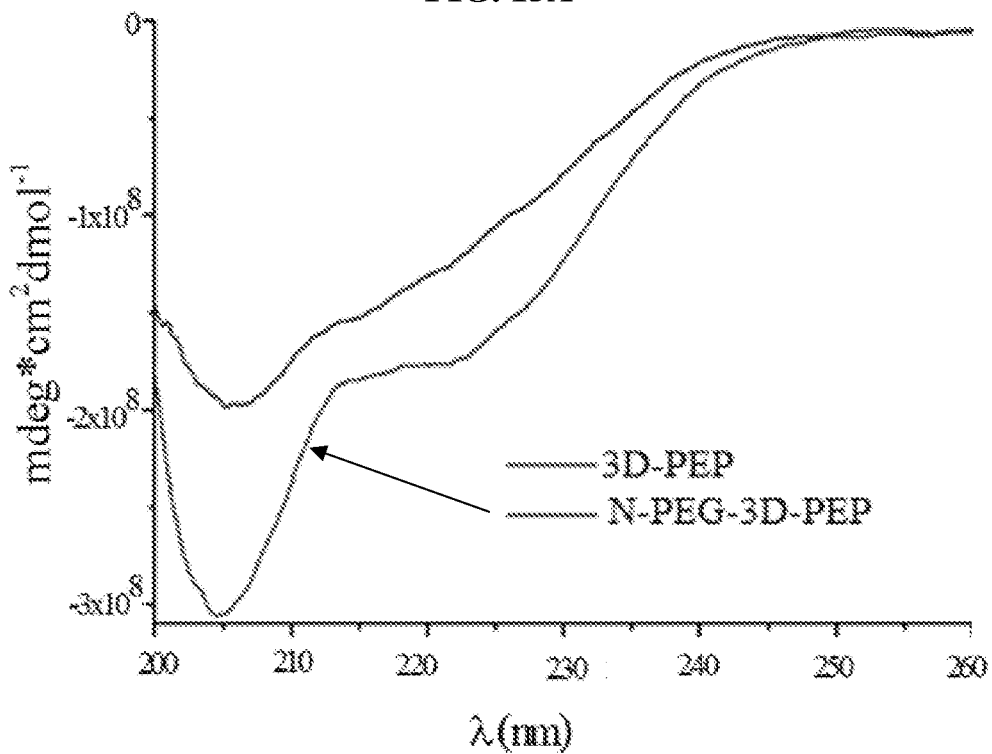
FIG. 15 shows a CD of PEG-N-3D-PEP (FIG. 15A) and PEG-C-3D-PEP (FIG. 15B).
Figure 15B:
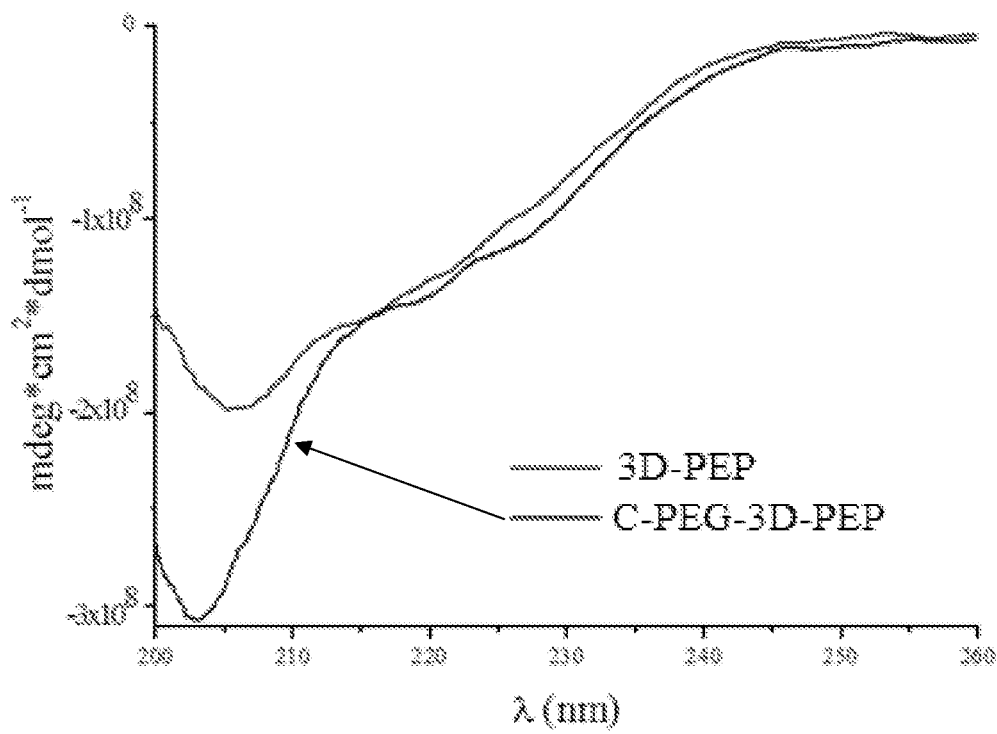

As follows from the CD analysis, both peptides had a helical nature (FIGS. 15A and 15B).

Figure 16A:
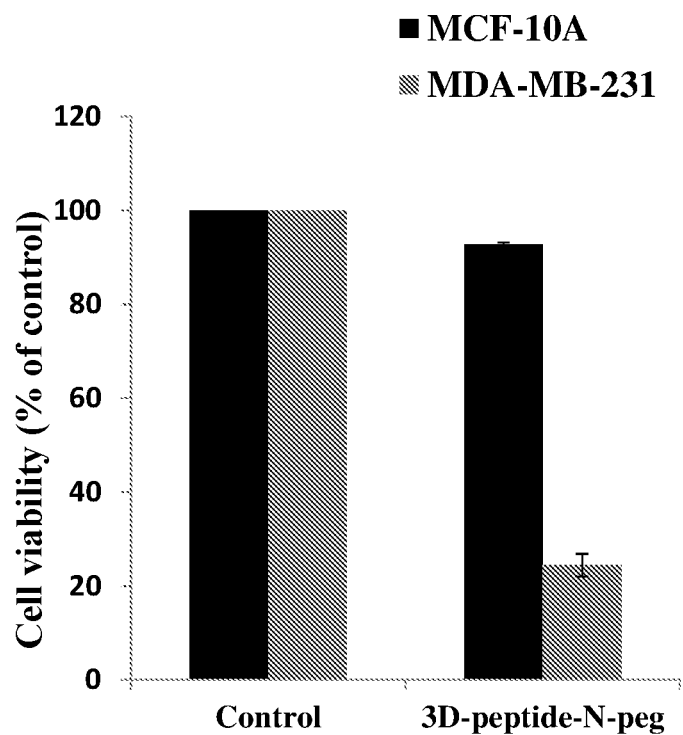
FIG. 16 shows the effect of PEG-N-3D-PEP (FIG. 16A) and PEG-C-3D-PEP (FIG. 16B) on the viability of non-malignant MCF-10A (left bars) or malignant MDA-MB-231 cells (right bars)
Figure 16B:
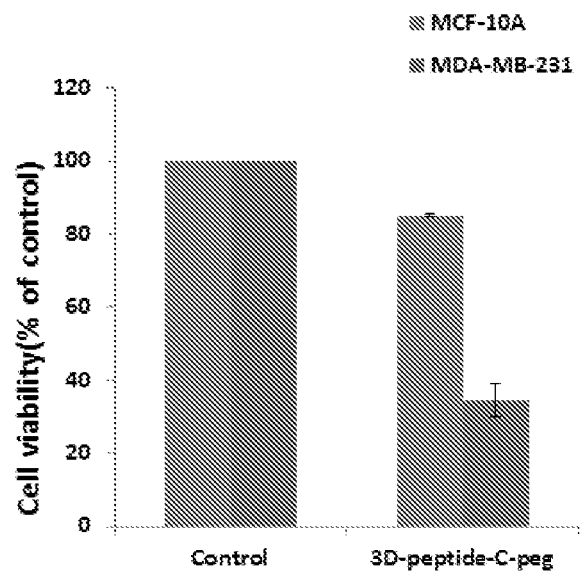

Cell viability of these two peptide conjugates were tested as well, using the method described in Example 1. It can be clearly seen that PEG-N-3D-PEP effectively reduced the viability of cancer cells by about 80%, (FIG. 16A, right bars, light gray) and that PEG-C-3D-PEP reduced the viability of cancer cells by about 70% (FIG. 16B, right bars, dark gray). In both cases, the conjugate had much weaker effect on the normal cells (FIG. 16). These results shows the selective toxicity of the PEGylated peptides to cancer cells.

Example 11. Stability of the Peptides and PEGylated Conjugates

Stability of the D-PEP, and 3D-PEP, analogs, and of PEG-N-3D-PEP and PEG-C-3D-PEP conjugates against protease cleavage (chymotrypsin and trypsin) was tested and compared to stability of the native peptide having SEQ ID NO: 1.

To peptides' stocks of 430 µl in concentration of 450 µM were added 0.001 mg/ml protease (Trypsin or Chymotrypsin) and incubated in room temperature (22° C.). Samples of 40 µl were taken before adding the protease and after every 15 min in the first hour, and after 2 h, 3 h, 4 h, 5 h, 7 h, 9 h and 24 h. To stop the proteolysis samples were added 7 µl of 2% TFA in TDW. The samples were added 60 µl TDW and were analyzed using analytical HPLC.

Figure 17A:
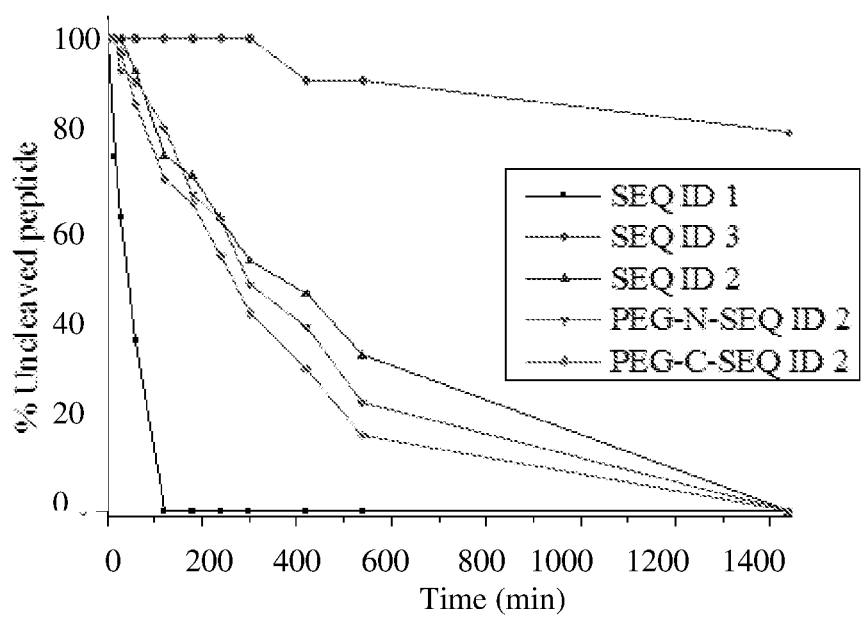
FIG. 17 shows the stability of different peptides to chymotrypsin (FIG. 17A) and trypsin (FIG. 17B) degradation.

The results are presented in FIG. 17 and show that while the native peptide having SEQ ID NO: 1 was rapidly and completely degraded by chymotrypsin already after about the 100 min, 3D-PEP and its PEG conjugates (either C-terminus or N-terminus) has a much longer half life. The D-PEP was the most stable to chymotrypsin degradation with only 20% of that peptide degraded after 1400 min (FIG. 17A).

Figure 17B:
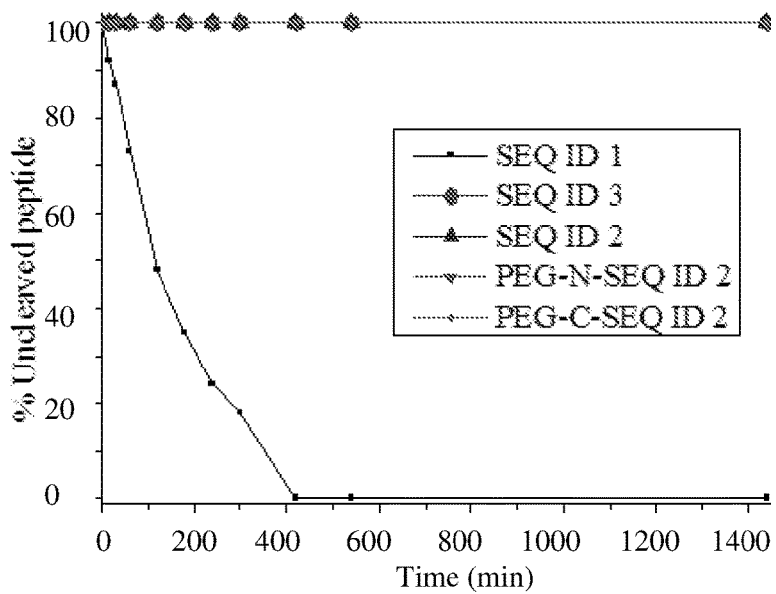

All peptides and conjugates except for the native one were stable for trypsin protease for at least 1400 min. The peptide having SEQ ID NO: 1 degraded completely after 400 min (FIG. 17B).

Although the present invention has been described herein above by way of preferred embodiments thereof, it can be modified, without departing from the spirit and nature of the subject invention as defined in the appended claims.

The invention claimed is:

1. A peptide comprising:
   (a) the amino acid sequence FLGVLALLGYLAVRPFLPKKKQQK set forth as SEQ ID NO: 1;
   (b) a retro-inverso sequence of (a) comprising the amino acid sequence kqqkkkplfprvalygllalvglf set forth as SEQ ID NO: 4;
   (c) an analog having at least 70% identity to the SEQ ID NO: 1 or SEQ ID NO: 4; or
   (d) a fragment consisting of 17 to 23 consecutive amino acids of (a), (b) or (c); wherein the peptide consists of 17 to 50 amino acids.

2. The peptide of claim 1, wherein the analog comprises 1 to 6 amino acid modifications to SEQ ID NO: 1.

3. The peptide of claim 2, wherein at least one modification is selected from the group consisting of: a conservative substitution of an amino acid residue; substitution of a lysine (Lys) residue for another positively charged amino acid; and substitution of at least one of the hydrophobic amino acids for an alanine (Ala) residue.

4. The peptide of claim 1, wherein the analog comprises at least one D-amino acid residue or wherein the analog consists of D-amino acid residues.

5. The peptide of claim 3, wherein at least one of the amino acid residues substituted with a D-amino acid residue is selected from an amino acid residue at position 10, 16 and 20 of SEQ ID NO: 1; or wherein the analog comprises the amino acid residues D-tyrosine, D-phenylalanine and D-lysine at positions 10, 16 and 20 of SEQ ID NO: 1, respectively.

6. The peptide of claim 5, comprising an amino acid sequence selected from the group consisting of: FLGVLALLGyLAVRPfLPKkKQQK set forth as SEQ ID NO: 2; and flgvlallgylavrpflpkkkqqk set forth as SEQ ID NO: 3.

7. The peptide of claim 1, comprising the amino acid sequence kqqkkkplfprvalygllalvglf set forth as SEQ ID NO: 4.

8. The peptide of claim 1, wherein the fragment consists of 17 to 23 consecutive amino acids of a sequence selected from SEQ ID NOs: 1, 2, 3 and 4.

9. The peptide of claim 1, wherein said peptide consists of an amino acid sequence selected from SEQ ID NOs: 1, 2, 3 and 4, analog of SEQ ID NO: 1 having at least 70% identity to the SEQ ID NO: 1, and a fragment thereof consisting of 17 to 23 consecutive amino acids.

10. The peptide of claim 1, comprising an amino acid sequence having at least 70% identity to the SEQ ID NO: 1 or SEQ ID NO: 4.

11. A conjugate of a peptide according to claim 1.

12. The conjugate of claim 11, wherein the peptide is conjugated with a polyethylene glycol (PEG) molecule.

13. The conjugate of claim 12, wherein the conjugate comprises a peptide consisting of SEQ ID NO: 2 and a PEG molecule comprising from 6 to 8 ethylene glycol monomers.

14. A pharmaceutical composition comprising at least one peptide of claim 1 or a conjugate thereof.

15. The pharmaceutical composition of claim 14, wherein the peptide consists of an analog of amino acid sequence selected from SEQ ID NOs: 1, 2, 3 and 4.

16. A method for treating cancer in a subject in need thereof comprising administering a peptide of claim 1 or a conjugate thereof.

17. The method of claim 16 wherein the cancer is associated with an enhanced expression of NAF-1 protein.

18. The method of claim 17, wherein the cancer is selected from the group consisting of a breast, prostate, gastric, cervical, liver, pancreas, head, neck and laryngeal cancer.

19. The method of claim 16, wherein the peptide or conjugate thereof are administered in combination with anti-cancer therapy.

* * * * *